United States Patent
Liu et al.

(10) Patent No.: US 8,969,332 B2
(45) Date of Patent: Mar. 3, 2015

(54) ARYLOXY DIHALOPROPENYL ETHER COMPOUNDS AND USES THEREOF

(75) Inventors: Changling Liu, Shenyang (CN); Jichun Yang, Shenyang (CN); Xiuhui Chang, Shenyang (CN); Miao Li, Shenyang (CN); KeKe Li, Shenyang (CN); Qiao Wu, Shenyang (CN); Yuquan Song, Shenyang (CN)

(73) Assignees: Sinochem Corporation, Beijing (CN); Shenyang Research Institute of Chemical Industry Co., Ltd., Shenyang (CN)

( * ) Notice: Subject to any disclaimer, the term of this patent is extended or adjusted under 35 U.S.C. 154(b) by 19 days.

(21) Appl. No.: 13/979,567

(22) PCT Filed: Mar. 28, 2012

(86) PCT No.: PCT/CN2012/073177
§ 371 (c)(1),
(2), (4) Date: Jul. 12, 2013

(87) PCT Pub. No.: WO2012/130137
PCT Pub. Date: Oct. 4, 2012

(65) Prior Publication Data
US 2013/0303541 A1 Nov. 14, 2013

(30) Foreign Application Priority Data
Mar. 30, 2011 (CN) ............................ 2011 1 0078669

(51) Int. Cl.
| | | |
|---|---|---|
| A61K 31/395 | (2006.01) |
| C07D 213/60 | (2006.01) |
| A01N 43/78 | (2006.01) |
| C07C 43/225 | (2006.01) |
| C07C 43/29 | (2006.01) |
| A01N 31/16 | (2006.01) |
| A01N 43/40 | (2006.01) |
| A01N 43/58 | (2006.01) |
| A01N 43/76 | (2006.01) |
| A01N 43/56 | (2006.01) |
| C07D 237/16 | (2006.01) |
| C07D 263/58 | (2006.01) |
| C07D 277/32 | (2006.01) |
| C07D 213/643 | (2006.01) |
| A01N 43/08 | (2006.01) |
| A01N 43/10 | (2006.01) |
| A01N 43/36 | (2006.01) |
| A01N 43/50 | (2006.01) |
| A01N 43/54 | (2006.01) |
| A01N 43/60 | (2006.01) |

(52) U.S. Cl.
CPC ............ *A01N 43/78* (2013.01); *C07C 43/225* (2013.01); *C07C 43/29* (2013.01); *A01N 31/16* (2013.01); *A01N 43/40* (2013.01); *A01N 43/58* (2013.01); *A01N 43/76* (2013.01); *A01N 43/56* (2013.01); *C07D 237/16* (2013.01); *C07D 263/58* (2013.01); *C07D 277/32* (2013.01); *C07D 213/643* (2013.01); *A01N 43/08* (2013.01); *A01N 43/10* (2013.01); *A01N 43/36* (2013.01); *A01N 43/50* (2013.01); *A01N 43/54* (2013.01); *A01N 43/60* (2013.01)
USPC .......................................... 514/183; 546/301

(58) Field of Classification Search
CPC ..................................................... A61K 31/395
See application file for complete search history.

(56) References Cited

U.S. PATENT DOCUMENTS

| | | | | |
|---|---|---|---|---|
| 2,267,587 A | * | 12/1941 | Fletcher et al. | ................ 514/751 |
| 4,448,968 A | | 5/1984 | Kristinsson | |
| 4,528,379 A | | 7/1985 | Cölln et al. | |
| 5,240,940 A | | 8/1993 | Arnold et al. | |
| 5,872,137 A | * | 2/1999 | Sakamoto et al. | ............ 514/345 |
| 5,922,880 A | | 7/1999 | Sakamoto et al. | |

(Continued)

FOREIGN PATENT DOCUMENTS

| | | |
|---|---|---|
| CN | 1137265 A | 12/1996 |
| CN | 1860874 A | 11/2006 |
| CN | 101056864 A | 10/2007 |
| EP | 0 344 684 A2 | 12/1989 |

(Continued)

OTHER PUBLICATIONS

University of Delaware. "Chlorinated Benzene." Available from: < http://www.math.udel.edu/~schleini/Mathlinks/Benzene/trial/benzene/node1.html >. Published online: Jun. 9, 1997.*

(Continued)

*Primary Examiner* — Noble Jarrell
*Assistant Examiner* — John S Kenyon
(74) *Attorney, Agent, or Firm* — Smith, Gambrell & Russell LLP

(57) ABSTRACT

The present invention discloses an aryloxy dihalopropenyl ether compound with the structure shown as general formula (I), of which the group definitions can be seen in the specification. The present invention also discloses the use of the compound with general formula (I) as an insecticide in the agricultural field and an insecticidal composition using the compound with general formula (I) as an active component.

(I)

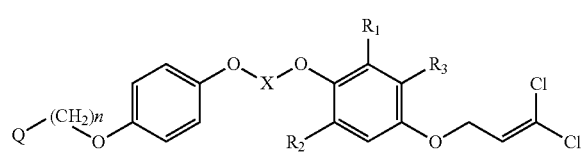

5 Claims, No Drawings

(56) References Cited

U.S. PATENT DOCUMENTS

| | | |
|---|---|---|
| 6,071,861 A | 6/2000 | Sakamoto et al. |
| 6,268,313 B1 | 7/2001 | Sakamoto et al. |
| 6,376,428 B1 | 4/2002 | Sakamoto et al. |
| 7,534,788 B2 | 5/2009 | Mohr et al. |
| 7,638,514 B2 | 12/2009 | Zambach et al. |
| 8,076,487 B2 | 12/2011 | Takabe et al. |
| 8,101,753 B2 | 1/2012 | Mizuno |
| 8,232,407 B2 | 7/2012 | Li et al. |
| 2003/0073847 A1 | 4/2003 | Sakamoto et al. |
| 2006/0148867 A1 | 7/2006 | Brown et al. |
| 2008/0280766 A1 | 11/2008 | Crowley et al. |
| 2009/0105308 A1 | 4/2009 | Mansfield et al. |
| 2010/0285957 A1 | 11/2010 | Kunz et al. |
| 2012/0088914 A1 | 4/2012 | Mizuno |

FOREIGN PATENT DOCUMENTS

| | | |
|---|---|---|
| EP | 2 281 812 A1 | 2/2011 |
| JP | 2004-346016 A | 12/2004 |
| JP | 2007-91596 A | 4/2007 |
| WO | 96/04228 A2 | 2/1996 |
| WO | 96/11909 A1 | 4/1996 |
| WO | 97/27173 A2 | 7/1997 |
| WO | 2005/019147 A2 | 3/2005 |
| WO | 2007/088876 A1 | 8/2007 |
| WO | 2009/013195 A1 | 1/2009 |
| WO | 2009/068652 A1 | 6/2009 |
| WO | 2009/083105 A1 | 7/2009 |

OTHER PUBLICATIONS

International Search Report for Application No. PCT/CN2012/073177 dated Jul. 5, 2012.

* cited by examiner

ARYLOXY DIHALOPROPENYL ETHER COMPOUNDS AND USES THEREOF

FIELD OF THE INVENTION

The present invention relates to insecticide. Specifically to an aryloxy dihalopropenyl ether compound and the uses thereof.

BACKGROUND OF THE INVENTION

It is well known that insects in general can cause significant damage, not only to crops grown in agriculture, but also, for example, to constructions and turf where the damage is caused by soil-borne insects (such as termites and white grubs). Such damage may result in the loss of millions of dollars concerning crop, turf or constructions. Insecticides are useful for controlling insects, but may cause significant damage to crops such as wheat, corn, soybeans, potatoes, and cotton. For crop protection, insecticides are desired which can control the insects while without damaging the crops, and have no deleterious effects to mammals and other living organisms.

The patent WO9604228 disclosed the compound 116 (D-1) having following general formula, which showed above 80% control against *Prodenia litura* at 500 ppm, and also showed above 80% control on *Heliothis virescens* at 100 ppm.

Compound 116

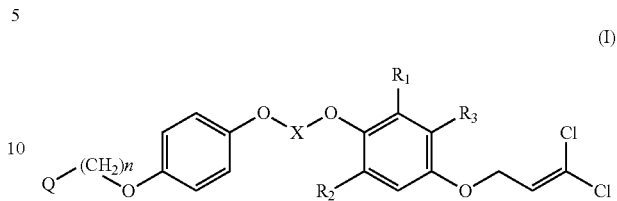

The patent WO9604228 disclosed some compounds with better insecticidal activity with above 80% control on *Plutella xylostella* at 50 ppm, especially the compound 36 (D-2) had been developed to be a commercial insecticide with common name of pyridalyl.

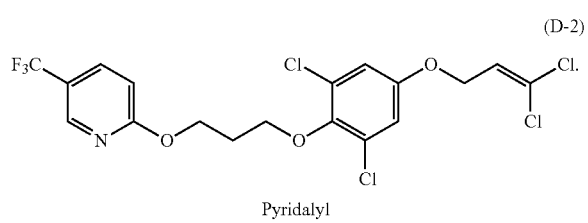 [SMILES: FC(F)(F)c1ccc(OCCCOc2c(Cl)cc(OCC=C(Cl)Cl)cc2Cl)nc1]

Pyridalyl

In the prior art, the compounds and their insecticidal activity having general formula of the present invention has not been reported.

SUMMARY OF THE INVENTION

The object of the present invention is to provide an aryloxy dihalopropenyl ether compound with novel structure and better insecticidal activity, which can be applied to prepare insecticides against insects in agriculture and other areas.

Detailed description of the invention is as follows:

The present invention provides an aryloxy dihalopropenyl ether compound having general formula (I):

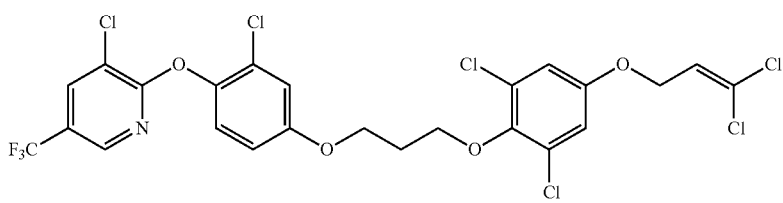

Wherein:

$R_1$, $R_2$, $R_3$ mutually independently may be the same or different, selected from H, halogen, $C_1$-$C_8$alkyl or $C_3$-$C_8$cycloalkyl;

X is selected from —$CH_2$—, —$CH_2CH_2$—, —$CH_2CH_2CH_2$—, —$CH_2CH_2CH_2CH_2$—, —$CH_2CH_2CH_2CH_2CH_2$—, —$CH(CH_3)$—, —$CH(CH_3)CH_2$—, —$CH(CH_3)CH_2CH_2$—, —$CH_2CH_2CH(CH_3)$—, —$CH(C_2H_5)$—, —$C(C_2H_5)_2$—, —$CH(CH_3)CH(CH_3)$—, —$CH_2C(CH_3)_2CH_2$—, —$CH_2CH_2OCH_2CH_2$—, —$CH_2CH_2NHCH_2CH_2$—, —$CH_2CH_2SCH_2CH_2$—, —$CH_2CH_2SO_2CH_2CH_2$—, —$CH_2CH(OH)CH_2$— or —$CH_2COCH_2$—;

Q is selected from aryl or heteroaryl, or above group substituted with 1-4 the same or different substitutents selected from halogen, CN, $NO_2$, OH, $C_1$-$C_8$alkyl, $C_3$-$C_8$cycloalkyl, $C_1$-$C_8$haloalkyl, $C_1$-$C_8$alkoxy, $C_1$-$C_8$haloalkoxy, $C_2$-$C_8$alkenyl, $C_2$-$C_8$alkynyl, $C_2$-$C_8$haloalkenyl, $C_2$-$C_8$haloalkynyl, $C_2$-$C_8$alkenyloxy, $C_2$-$C_8$alkynyloxy, $C_2$-$C_8$haloalkenyloxy, $C_2$-$C_8$haloalkynyloxy, aryl, $COR_5$, $CO_2R_4$, $CONR_4R_5$, $NR_4R_5$, $NR_4COR_5$, $NR_5COR_4$, $NR_5CO_2R_4$, $NR_5SO_2R_4$, $SOR_5$, $SO_2R_5$, $SR_5$ or $SO_2NR_4R_5$;

$R_4$ is selected from H, $C_1$-$C_8$alkyl, $C_1$-$C_8$haloalkyl or $C_3$-$C_8$cycloalkyl;

$R_5$ is selected from H, $C_1$-$C_8$alkyl, $C_1$-$C_8$haloalkyl $C_3$-$C_8$cycloalkyl, unsubstituted aryl or substituted aryl, unsubstituted heteroaryl or substituted heteroaryl, on which there are 1-4 the same or different substitutents selected from halogen, CN, $NO_2$, $C_1$-$C_8$alkyl, $C_1$-$C_8$haloalkyl, $C_1$-$C_8$alkoxy, $C_1$-$C_8$haloalkoxy, $C_1$-$C_8$alkoxycarbonyl or $C_1$-$C_8$alkylsulfonyl;

n is selected from 0, 1 or 2.

The preferred compounds of general formula I of the invention are:

$R_1$, $R_2$, $R_3$ mutually independently may be the same or different, selected from H or halogen;

X is selected from —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH(OH)CH_2$— or —$CH_2COCH_2$—;

Q is selected from aryl or heteroaryl, or above group substituted with 1-4 the same or different substituents selected from halogen, CN, $NO_2$, OH, $C_1$-$C_8$alkyl, $C_3$-$C_8$cycloalkyl, $C_1$-$C_8$haloalkyl, $C_1$-$C_8$alkoxy, $C_1$-$C_8$haloalkoxy, $C_2$-$C_8$alkenyl, $C_2$-$C_8$alkynyl, $C_1$-$C_8$haloalkenyl, $C_2$-$C_8$haloalkynyl, $C_2$-$C_8$alkenyloxy, $C_2$-$C_8$alkynyloxy, $C_2$-$C_8$haloalkenyloxy, $C_2$-$C_8$haloalkynyloxy, $CO_2R_4$, $NR_5SO_2R_4$, $SO_2R_5$ or $SR_5$;

$R_4$ is selected from H, $C_1$-$C_4$alkyl, $C_1$-$C_4$haloalkyl or $C_3$-$C_6$cycloalkyl;

$R_5$ is selected from H, $C_1$-$C_4$alkyl, $C_1$-$C_4$haloalkyl or $C_3$-$C_6$cycloalkyl;

n is selected from 0, 1 or 2.

Further more, the preferred compounds of general formula (I) of this invention are:

$R_1$, $R_2$, $R_3$ mutually independently may be the same or different, selected from H, Cl or Br;

X is selected from —$CH_2$—, —$CH_2CH_2$—, —$CH_2CH_2CH_2$—, —$CH_2CH_2CH_2CH_2$— or —$CH_2CH_2CH_2CH_2CH_2$—;

Q is selected from pyrrolyl, furyl, thienyl, imidazolyl, pyrazolyl, oxazolyl, thiazolyl, isoxazolyl, isothiazolyl, phenyl, pyridinyl, pyrimidinyl, pyridazinyl, pyrazinyl, pyridazinoneyl, indolyl, benzofuranyl, benzoxazolyl, benzothienyl, benzothiazolyl, benzisoxazolyl, benzisothiazolyl, benzimidazolyl, benzopyrazolyl or quinoxalinyl, or above group substituted with 1-3 substitutents mutually independently selected from halogen, CN, $NO_2$, OH, $C_1$-$C_8$alkyl, $C_3$-$C_8$cycloalkyl, $C_1$-$C_8$haloalkyl, $C_1$-$C_8$alkoxy, $C_1$-$C_8$haloalkoxy, $C_1$-$C_4$alkylthio, $C_2$-$C_6$alkenyl, $C_2$-$C_6$alkynyl, $C_2$-$C_6$haloalkenyl, $C_2$-$C_6$haloalkynyl, $C_2$-$C_6$alkenyloxy, $C_2$-$C_6$alkynyloxy, $C_2$-$C_6$haloalkenyloxy or $C_2$-$C_6$haloalkynyloxy;

n is selected from 0 or 10

Even more preferred compounds of general formula (I) of this invention are:

$R_1$, $R_2$, $R_3$ mutually independently may be the same or different, selected from H or Cl;

X is selected from —$CH_2$—, —$CH_2CH_2$—, —$CH_2CH_2CH_2$— or —$CH_2CH_2CH_2CH_2$—;

Q is selected from imidazolyl, pyrazolyl, oxazolyl, thiazolyl, isoxazolyl, isothiazolyl, phenyl, pyridinyl, pyrimidinyl, pyridazinyl, pyridazinoneyl, indolyl, benzofuranyl, benzoxazolyl, benzothiazolyl, benzisoxazolyl, benzisothiazolyl, benzimidazolyl, benzopyrazolyl or quinoxalinyl, or above group substituted with 1-3 substitutents mutually independently selected from halogen, CN, $NO_2$, OH, $C_1$-$C_4$alkyl, $C_3$-$C_6$cycloalkyl, $C_1$-$C_4$haloalkyl, $C_1$-$C_4$alkoxy, $C_1$-$C_4$haloalkoxy, $C_1$-$C_4$alkylthio, $C_2$-$C_4$alkenyl, $C_2$-$C_4$alkynyl, $C_2$-$C_4$haloalkenyl, $C_2$-$C_4$haloalkynyl, $C_2$-$C_4$alkenyloxy, $C_2$-$C_4$alkynyloxy, $C_2$-$C_4$haloalkenyloxy or $C_2$-$C_4$haloalkynyloxy;

n is selected from 0 or 1.

Even more compounds of general formula (I) of the invention are:

$R_1$, $R_2$, $R_3$ mutually independently may be the same or different, selected from H or Cl;

X is selected from —$CH_2$—, —$CH_2CH_2$—, —$CH_2CH_2CH_2$— or —$CH_2CH_2CH_2CH_2$—;

Q is selected from thiazolyl, phenyl, pyridinyl, pyrimidinyl, pyridazinyl, pyridazinoneyl, benzoxazolyl, benzisothiazolyl or quinoxalinyl, or above group substituted with 1-3 substitutents mutually independently selected from F, Cl, Br, I, CN, $NO_2$, OH, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_2$-$C_4$alkenyl, $C_2$-$C_4$alkynyl, $C_2$-$C_4$haloalkenyl, $C_2$-$C_4$haloalkynyl, $C_2$-$C_4$alkenyloxy or $C_2$-$C_4$alkynyloxy;

n is selected from 0 or 1.

Even more compounds of general formula (I) of the invention are:

$R_1$, $R_2$, $R_3$ mutually independently may be the same or different, selected from H or Cl;

X is —$CH_2CH_2CH_2$—;

Q is selected from thiazolyl, phenyl, pyridinyl, pyrimidinyl, pyridazinyl, pyridazinoneyl, benzoxazolyl, benzisothiazolyl or quinoxalinyl, or above group substituted with 1-3 substitutents mutually independently selected from F, Cl, Br, CN, $NO_2$, $CH_3$, $C_2H_5$, $C(CH_3)_3$, $CF_3$, $CHFCH_3$, $CHF_2$, $OCH_3$, $OCF_3$, $OCHF_2$ or $SCH_3$;

n is selected from 0 or 1.

The most preferred compounds of general formula (I) of the invention are:

$R_1$, $R_2$, $R_3$ mutually independently may be the same or different, selected from H or Cl;

X is —$CH_2CH_2CH_2$—;

Q is selected from thiazolyl, phenyl, pyridinyl, pyridazinoneyl or benzoxazolyl, or above group substituted with 1-3 substitutents mutually independently selected from F, Cl, Br, $CH_3$, $C_2H_5$, $C(CH_3)_3$, $CF_3$, $CHFCH_3$ or $CHF_2$;

n is selected from 0 or 1.

The terms used above to definite the compounds having general formula (I) represent substitutes as follow:

Halogen or halo is fluorine, chlorine, bromine or iodine. The alkyl is to be understood as meaning straight or branched chain alkyl, such as methyl, ethyl, n-propyl, i-propyl, n-butyl, or the different butyl, pentyl or hexyl isomers. Cycloalkyl is monocyclic saturated hydrocarbonyl groups having 3 to 8 carbon atoms, such as cyclopropyl, cyclobutyl, cyclopentyl or cycloheyl etc. The haloalkyl stands for straight or branched chain alkyl, in which hydrogen atoms can be all or partly substituted with halogen, such as chloromethyl, dichloromethyl, trichloromethyl, fluoromethyl, difluoromethyl, trifluoromethyl or heptafluoroisopropyl, etc. The alkoxy refers to straight or branched chain alkyl, which is linked to the structure by oxygen atom. such as $OCH_3$, $OC_2H_5$ or $OC(CH_3)_3$. The haloalkoxy refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy; trifluoroethoxy, etc. The alkenyl refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl. The alkynyl refers to straight or branched chain alkynyl, such as ethynyl, 1-propynyl and different isomer of butynyl, pentynyl and hexynyl. Alkynyl also includes groups including more than one triple bonds, such as hexa-2,5-diynyl. The haloalkenyl stands for straight or branched chain alkenyl, in which hydrogen atoms can be all or partly substituted with halogen. The haloalkynyl stands for straight or branched chain alkynyl, in which hydrogen atoms can be all or partly substituted with halogen. The alkoxycarbonyl is alkyl-O—CO. The alkenoxyl refers to straight or branched chain alkynes is linked to the structure by oxygen, such as propenyloxy. The alkynoxyl refers to straight or branched chain alkynes is linked to the structure by oxygen, such as propynyloxy. The haloalkenoxyl stands for a straight-chain or branched alkenoxyl, in which hydrogen atoms may be all or partly substituted with halogen. The haloalkynoxyl stands for a straight-chain or branched alkynoxyl, in which hydrogen atoms may be all or partly substituted with halogen. The alkylamino refers to straight or branched chain alkyl, which is linked to the structure by nitrogen atom. Alkylamino, for example, methylatnino, ethylamino, n-propylamino, isopropylamino or the isomeric butylamines. Alkylsulfonyl is Alkyl-S(O)$_2$—.

The aryl includes phenyl or naphthyl etc.

The heteroaryl stands for five member ring or six member ring containing one or more N, O, S hetero atoms. Such as pyrrolyl, furyl, thienyl, imidazolyl, pyrazolyl, oxazolyl, thiazolyl, isoxazolyl, isothiazolyl, pyridinyl, pyrimidinyl, pyridazinyl, pyridazinoneyl, indolyl, benzofuranyl, benzoxazolyl, benzothienyl, benzothiazolyl, benzisoxazolyl, benzisothiazolyl, benzimidazolyl, benzopyrazolyl or quinoxalinyl etc.

Some preferred substitutes of Q in formula (I) of the invention are listed in Tables 1-15:

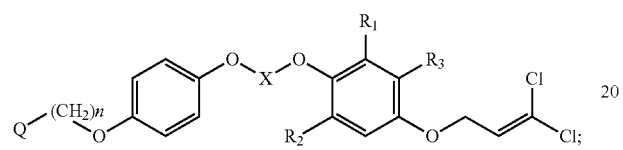

(I)

The definitions of other substituents in formula (I) are as defined above.

When Q is pyridinyl, the substituted groups on pyridinyl ring refer to Tables 1-3. When Q is phenyl, the substituted groups on phenyl ring refer to Table 4. When Q is pyrimidinyl, the substituted groups on pyrimidinyl ring refer to Tables 5-6. When Q is pyrazinyl or quinoxalinyl, the substituted groups of ring refer to Table 7. When Q is pyridazinyl, the substituted groups on pyridazinyl ring refer to Table 8. When Q is pyrazolyl, the substituted groups on pyrazolyl ring refer to Tables 9-10. When Q is thiazolyl, oxazolyl, imidazolyl, benzothiazolyl, benzimidazolyl or benzoxazolyl, the substituted groups of ring refer to Tables 11-12. When Q is thienyl, pyrrolyl, furyl, benzothienyl, indolyl or benzofuranyl, the substituted groups of ring refer to Tables 13-14. When Q is pyridazinoneyl, the substituted groups on pyridazinoneyl ring refer to Table 15.

TABLE 1

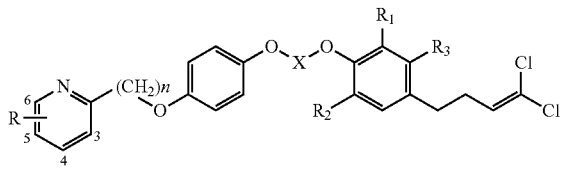

| R | R |
|---|---|
| 3-CH$_3$ | 3-CO$_2$CH$_3$ |
| 4-CH$_3$ | 5-CO$_2$CH$_3$ |
| 5-CH$_3$ | 3,5-2Cl-6-OCH$_3$ |
| 6-CH$_3$ | 5-CF$_3$-3-Cl |
| 3-Cl | 5-CN-3-Cl |
| 4-Cl | 5-CH$_3$-3-Cl |
| 5-Cl | 3-CH$_3$-5-NO$_2$ |
| 6-Cl | 4-CH$_3$-3-NO$_2$ |
| 3-CF$_3$ | 4-CH$_3$-5-NO$_2$ |
| 4-CF$_3$ | 5-CH$_3$-3-NO$_2$ |
| 5-CF$_3$ | 6-CH$_3$-4-NO$_2$ |
| 6-CF$_3$ | 6-CH$_3$-5-NO$_2$ |
| 3-Br | 3-NO$_2$-5-Cl |
| 4-Br | 3-NO$_2$-5-Br |
| 5-Br | 5-NO$_2$-3-Br |
| 6-Br | 5-CH$_3$-3-Br |
| 5-I | 6-CH$_3$-5-Br |
| 5-F | 3-CH$_3$-5-Br |
| 6-F | 3-CF$_3$-6-Cl |
| 3-CN | 6-CH$_3$-3,5-2Br |
| 4-CN | 3-CONH$_2$-4,6-2Cl |
| 5-CN | 4-CH$_3$-5-NO$_2$-3-Br |
| 6-CN | 3-CN-4,6-2Cl |
| 3-NO$_2$ | 3-CN-4-CH$_3$-6-Cl |
| 5-NO$_2$ | 3-CN-4-CF$_3$-6-Cl |
| 6-NO$_2$ | 4-CH$_3$-5-CN-6-Cl |
| 6-OCH$_3$ | 4-CF$_3$-5-CN-6-Cl |
| 5-OCH$_3$ | 3-CO$_2$CH$_3$-6-Cl |
| 3,5-2Cl | 5-CO$_2$CH$_3$-6-Cl |
| 3,5-2Br | 5-CF$_3$-3,6-2Cl |
| 4-CH$_3$-5-Br | 5-CF$_3$-6-Cl |
| 6-CH$_3$-5-CN | 3-CN-6-Cl |
| 3,5,6-3Cl | |

TABLE 2

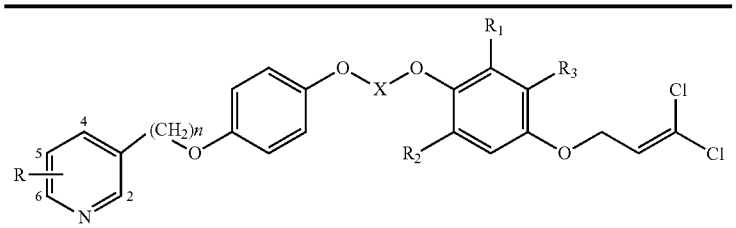

| R |
|---|
| 5-Cl |
| 2-Cl |
| 6-Cl |
| 2-Br |
| 6-Br |
| 2-CH$_3$ |
| 2-CN |
| 6-CF$_3$ |
| 4-CF$_3$ |
| 4-CH$_3$ |
| 2-OCH$_3$ |
| 2,5-2Cl |
| 2,6-2Cl |
| 5,6-2Cl |
| 6-CH$_3$ |
| 2,4-2Cl |

TABLE 2-continued
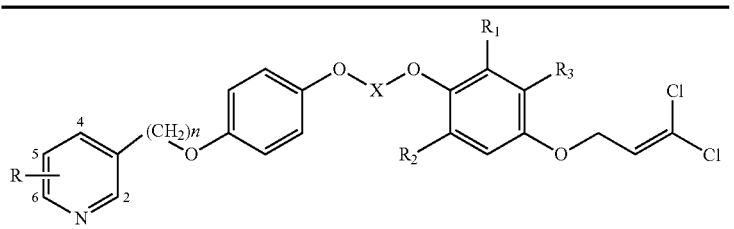
| R |
|---|
| 6-CN |
| 2-OCHF$_2$ |
| 2-CF$_3$ |
| 5-CH$_3$-2-Cl |
| 4-CH$_3$-2-Cl |
| 6-OCH$_3$ |
| 6-CH$_3$-2-Cl |
| 2-OCH$_2$CF$_3$ |
| 6-OCHF$_2$ |
| 6-OCH$_2$CF$_3$ |
| 5-Cl-2-CN |
| 6-CF$_3$-2-Cl |
| 6-SO$_2$CH$_3$-5-Cl |
| 6-NHCH$_3$-5-Cl |
| 6-OCH$_3$-2-Cl |
| 4-CF$_3$-2,6-2Cl |
| 4-CH$_3$-2,6-2Cl |
| 6-CH$_3$-2,4-2Cl |
| 6-CF$_3$-2,4-2Cl |
TABLE 3
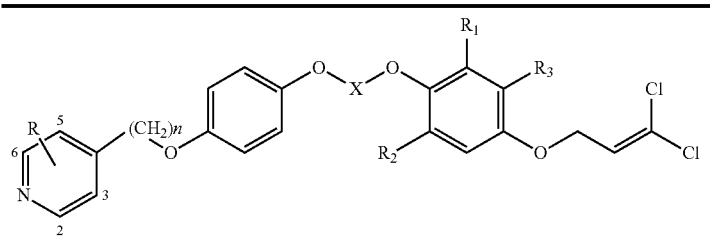
| R |
|---|
| 2-F |
| 2-Cl |
| 2-Br |
| 2-I |
| 3-Cl |
| 3-Br |
| 3-NO$_2$ |
| 2-CN |
| 3-CN |
| 2-CF$_3$ |
| 2-CH$_3$ |
| 2-OCH$_3$ |
| 2-OCHF$_2$ |
| 2-OCF$_3$ |
| 2,6-2Cl |
| 3,5-2Cl |
| 2-Cl-3-CN |
| 3,5-2OCH$_3$ |
| 3-CN-2-OCH$_3$ |
| 2-Cl-3-NO$_2$ |
| 2-Cl-3-CN-6-CH$_3$ |
| 2,6-2OCH$_3$ |
| 2-OC(CH$_3$)$_3$ |
| 2-OCH$_2$CF$_3$ |
| 2-Cl-5-NO$_2$ |
| 2-Cl-3,5-2NO$_2$ |
| 2,6-2F |
| 2-OCH$_3$-6-Cl |
| 2-NHCH$_3$-6-Cl |

TABLE 3-continued

![Structure with pyridine ring bearing R at positions 5,6, (CH2)n linker to phenyl-O-X-O-phenyl(R1,R2,R3)-O-CH2-CH=CCl2]

| R |
|---|
| 3-Cl-6-NO₂ |
| 5,6-(CH=CH—CH=CH—) |
| 2,3-2CH₃-5,6-(CH=CH—CH=CH—) |
| 2-CH₃-5,6-(CH=CH—CH=CH—) |
| 2-CF₃-5,6-(CH=CH—CH=CH—) |
| 2,3-2CH₃-4,5-(CH=CF—CH=CF—) |
| 2,3-2CH₃-5,6-(CH=CF—CH=CF—) |
| 2-CF₃-5,6-(CH=CF—CH=CH—) |
| 2-CH₃-5,6-(CH=CF—CH=CH—) |
| 5,6-(CH=CF—CH=CF—) |
| 5,6-(CH=Cl—CH=CH—) |

TABLE 4

![Structure with phenyl ring bearing R at positions 2-6, (CH2)n linker to phenyl-O-X-O-phenyl(R1,R2,R3)-O-CH2-CH=CCl2]

| R |
|---|
| 4-CN |
| 2-F |
| 3-F |
| 4-F |
| 2-Cl |
| 3-Cl |
| 4-Cl |
| 2-Br |
| 3-Br |
| 4-Br |
| 2-I |
| 3-I |
| 4-I |
| 2-CH₃ |
| 3-CH₃ |
| 4-CH₃ |
| 2-C₂H₅ |
| 3-C₂H₅ |
| 4-C₂H₅ |
| 2-CF₃ |
| 3-CF₃ |
| 4-CF₃ |
| 2-OCH₃ |
| 3-OCH₃ |
| 4-OCH₃ |
| 2-SCH₃ |
| 3-SCH₃ |
| 4-SCH₃ |
| 2-OCF₃ |
| 3-OCF₃ |
| 4-OCF₃ |
| 2-CN |
| 3-CN |
| 4-CN |
| 4-NO₂ |
| 2-CN |

TABLE 4-continued

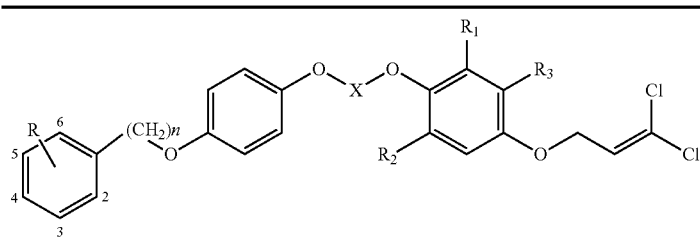

| R |
|---|
| 3-SCF$_3$ |
| 4-SCF$_2$ |
| 2-OC$_2$H$_5$ |
| 3-OC$_2$H$_5$ |
| 4-OC$_2$H$_5$ |
| 2-O(CH$_3$)$_3$ |
| 3-O(CH$_3$)$_3$ |
| 4-O(CH$_3$)$_3$ |
| 2-OCHF$_2$ |
| 2-C(CH$_3$)$_3$ |
| 3-C(CH$_3$)$_3$ |
| 4-C(CH$_3$)$_3$ |
| 2-COCH$_3$ |
| 3-COCH$_3$ |
| 4-COCH$_3$ |
| 2-COC$_2$H$_5$ |
| 3-COC$_2$H$_5$ |
| 4-COC$_2$H$_5$ |
| 2-SOCH$_3$ |
| 3-SOCH$_3$ |
| 4-SOCH$_3$ |
| 2-SO$_2$CH$_3$ |
| 3-SO$_2$CH$_3$ |
| 4-SO$_2$CH$_3$ |
| 2-SOC$_2$H$_5$ |
| 3-SOC$_2$H$_5$ |
| 4-SOC$_2$H$_5$ |
| 3-OCHF$_2$ |
| 4-OCHF$_2$ |
| 2,3-2NO$_2$ |
| 2-NO$_2$ |
| 3-NO$_2$ |
| 2-SO$_2$CH$_2$H$_5$ |
| 3-SO$_2$CH$_2$H$_5$ |
| 4-SO$_2$CH$_2$H$_5$ |
| 2-CO$_2$CH$_3$ |
| 3-CO$_2$CH$_3$ |
| 4-CO$_2$CH$_3$ |
| 2-CO$_2$C$_2$H$_5$ |
| 3-CO$_2$C$_2$H$_5$ |
| 4-CO$_2$C$_2$H$_5$ |
| 2-N(CH$_3$)$_3$ |
| 3-N(CH$_3$)$_3$ |
| 4-N(CH$_3$)$_3$ |
| 2-N(C$_2$H$_5$)$_3$ |
| 3-N(C$_2$H$_5$)$_3$ |
| 4-N(C$_2$H$_5$)$_3$ |
| 2,3-2OCH$_3$ |
| 2,4-2OCH$_3$ |
| 2,5-2OCH$_3$ |
| 2,6-2OCH$_3$ |
| 3,4-2OCH$_3$ |
| 3,5-2OCH$_3$ |
| 3-CONH$_2$ |
| 4-CONH$_2$ |
| 2,4-2NO$_2$ |
| 2,5-2NO$_2$ |
| 2,6-2NO$_2$ |
| 3,4-2NO$_2$ |
| 3,5-2NO$_2$ |
| 2,3,6-3F |
| 2,4,5-3F |
| 2,4,6-3F |
| 2,3,4-3F |
| 2,3,5-3F |
| 4-F-6-Cl |

TABLE 4-continued
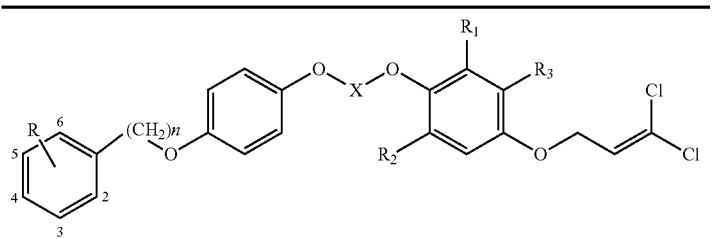
| R |
|---|
| 2,3-2F |
| 2,4-2F |
| 2,5-2F |
| 2,6-2F |
| 3,4-2F |
| 3,5-2F |
| 2,3-2Cl |
| 2,4-2Cl |
| 2,5-2C |
| 2,6-2Cl |
| 3,4-2Cl |
| 3,5-2Cl |
| 2,3-2Br |
| 2,4-2Br |
| 2,5-2Br |
| 2,6-2Br |
| 3,4-2Br |
| 3,5-2Br |
| 2,3-2CN |
| 2,4-2CN |
| 2,5-2CN |
| 2,6-2CN |
| 3,4-2CN |
| 3,5-2CN |
| 2-F-4-Cl |
| 2-F-4-Br |
| 2-F-4-I |
| 2-F-5-Cl |
| 3-F-5-Cl |
| 4-F-3-Cl |
| 2,3-2CF$_3$ |
| 2,4-2CF$_3$ |
| 2,5-2CF$_3$ |
| 2,6-2CF$_3$ |
| 2,3-2CH$_3$ |
| 2,4-2CH$_3$ |
| 2,5-2CH$_3$ |
| 2,6-2CH$_3$ |
| 3,4-2CH$_3$ |
| 3,5-2CH$_3$ |
| 2,3-2C$_2$H$_5$ |
| 2,4-2C$_2$H$_5$ |
| 2,5-2C$_2$H$_5$ |
| 2,6-2C$_2$H$_5$ |
| 3,4-2C$_2$H$_5$ |
| 3,5-2C$_2$H$_5$ |
| 3,4-2CF$_3$ |
| 3,5-2CF$_3$ |
| 2,6-2SCF |
| 3,4-2SCF$_3$ |
| 3,5-2SCF$_3$ |
| 2,3-2SCH$_3$ |
| 2,4-2SCH$_3$ |
| 2,5-2SCH$_3$ |
| 2,6-2SCH$_3$ |
| 3,4-2SCH$_3$ |
| 3,5-2SCH$_3$ |
| 2,3-2OCF$_3$ |
| 2,4-2OCF$_3$ |
| 2,5-2OCF$_3$ |
| 2,6-2OCF$_3$ |
| 3,4-2OCF$_3$ |
| 3,5-2OCF$_3$ |
| 2,3-2SCF$_3$ |
| 2,4-2SCF$_3$ |
| 2,5-2SCF$_3$ |

TABLE 4-continued

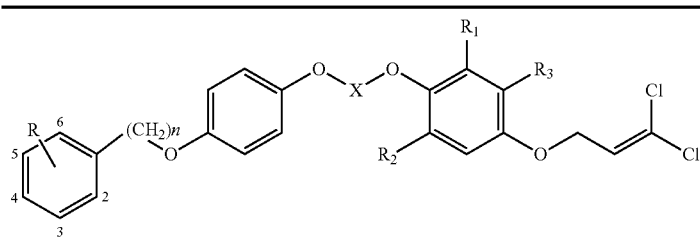

| R |
|---|
| 2,4,6-3CF$_3$ |
| 3,4,5-3Br |
| 2-Cl-4-F |
| 2-Cl-4-Br |
| 2-Cl-4-I |
| 3-Cl-4-I |
| 4-Cl-2-Br |
| 3,4,5-3F |
| 2,3,4-3Cl |
| 2,3,5-3Cl |
| 2,3,6-3Cl |
| 2,4,5-3Cl |
| 2,4,6-3Cl |
| 3,4,5-3Cl |
| 2,3,4-3Br |
| 2,3,5-3Br |
| 2,3,6-3Br |
| 2,4,5-3Br |
| 2,4,6-3Br |
| 4-CH$_3$-3-F |
| 4-CH$_3$-3-Cl |
| 4-CH$_3$-3-Br |
| 2-CH$_3$-3-F |
| 2-CH$_3$-3-Cl |
| 2-CH$_3$-4-F |
| 2-CH$_3$-4-Cl |
| 2-CH$_3$-4-Br |
| 2-CH$_3$-5-F |
| 2-CH$_3$-5-Cl |
| 2-CH$_3$-5-Br |
| 2-CH$_3$-6-Cl |
| 3-CH$_3$-2-Br |
| 3-CH$_3$-4-Cl |
| 3-CH$_3$-4-Br |
| 3-CH$_3$-4-I |
| 2-CH$_3$-4-I |
| 4-CH$_3$-2-Br |
| 4-CH$_3$-2-Cl |
| 2,4,6-3CH$_3$ |
| 2,4,6-3C$_2$H$_5$ |
| 2-NHCOCH$_3$ |
| 3-NHCOCH$_3$ |
| 4-NHCOCH$_3$ |
| 2-NHSO$_2$CH$_3$ |
| 3-NHSO$_2$CH$_3$ |
| 4-NHSO$_2$CH$_3$ |
| 2-CH(CH$_3$)$_2$ |
| 3-CH(CH$_3$)$_2$ |
| 4-CH(CH$_3$)$_2$ |
| 2-CF$_3$-4-Cl |
| 2-CF$_3$-4-Br |
| 3-CF$_3$-4-NO$_2$ |
| 3-CF$_3$-4-F |
| 3-CF$_3$-4-Cl |
| 4-CF$_3$-2-NO$_2$ |
| 4-CF$_3$-2-Cl |
| 4-CF$_3$-2-Br |
| 2-CH$_3$-5-NO$_2$ |
| 2-CH$_3$-3-NO$_2$ |
| 2-SCH$_3$-5-Cl |
| 4-SO$_2$CH$_3$-2-Cl |
| 2-CH$_3$-4-NO$_2$ |
| 2-CH$_3$-4-OCH$_3$ |
| 2-CH$_3$-6-C$_2$H$_5$ |
| 2-CH$_3$-6-NO$_2$ |
| 2,4,6-3NO$_2$ |

TABLE 4-continued

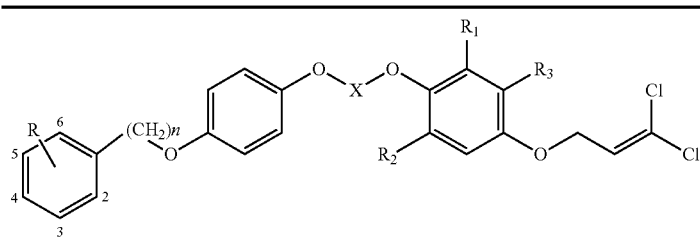

| R |
|---|
| 2,3-2Cl-4-Br |
| 2,4-2F-6-Cl |
| 2-NO$_2$-4,6-2Br |
| 2-NO$_2$-4-F |
| 2-CN-3-F |
| 2-CN-3-Cl |
| 2-CN-4-Cl |
| 2-CN-4-Br |
| 5-CH$_3$-2-F |
| 4-CN-2-Cl |
| 2-F-3-Cl |
| 2,3,5,6-4F |
| 5-CF$_3$-2-Cl |
| 5-CF$_3$-2-Br |
| 2-CN-4-NO$_2$ |
| 4-CN-2-CF$_3$ |
| 4-CN-2-NO$_2$ |
| 5-NO$_2$-2-F |
| 2-NO$_2$-6-Cl |
| 2-NO$_2$-4-Cl |
| 2-NO$_2$-4-Br |
| 2-NO$_2$-5-Cl |
| 3-NO$_2$-4-Cl |
| 3-NO$_2$-4-Br |
| 4-NO$_2$-2-Cl |
| 5-NO$_2$-2-Cl |
| 5-NO$_2$-2-Br |
| 3-NO$_2$-4-F |
| 4-SO$_2$NH$_2$ |
| 2,4,6-3OCH$_3$ |
| 3,4,5-3OCH$_3$ |
| 2,4,6-3SCH$_3$ |
| 2,4,6-3OCF$_3$ |
| 2,4,6-3SCF$_3$ |
| 3-CH$_3$-2-Cl |
| 2,3-2C(CH$_3$)$_2$ |
| 2,4-2C(CH$_3$)$_2$ |
| 2,5-2C(CH$_3$)$_3$ |
| 2,6-2C(CH$_3$)$_3$ |
| 3,4-2C(CH$_3$)$_3$ |
| 3,5-2C(CH$_3$)$_3$ |
| 4-O(CH$_2$)$_3$CH$_3$ |
| 2-CN-4,6-2Cl |
| 2-CN-4,6-2Br |
| 2-CF$_3$-4-NO$_2$ |
| 5-CONH$_2$-2-Cl |
| 4-CH$_3$-2-NO$_2$ |
| 4-CH$_3$-3-NO$_2$ |
| 5-CH$_3$-2-CN |
| 2-CF$_3$-4,6-2Cl |
| 2-CF$_3$-4,6-2Br |
| 3-CH$_3$-2,6-2Cl |
| 2-CH$_3$-4,6-2Br |
| 2-CH$_2$C≡CH |
| 3-CH$_2$C≡CH |
| 4-CH$_2$C≡CH |
| 2-OCH$_3$-5-Cl |
| 4-OCH$_3$-3-F |
| 4-OCH$_3$-3-Cl |
| 2-OCF$_3$-4-CN |
| 2-OCF$_3$-4-Cl |
| 2-OCF$_3$-4-Br |
| 2-F-4,6-2Br |
| 4-OCF$_3$-2-Cl |
| 4-OCF$_3$-2-Br |
| 4-F-2,6-2Br |

TABLE 4-continued

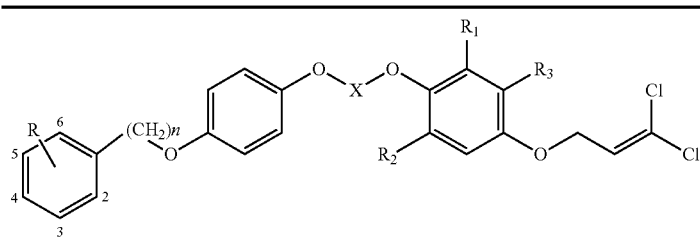

| R |
|---|
| 2,4-2F-6-Cl |
| 4-NO$_2$-2-OCH$_3$ |
| 2-CH$_2$CH=CH$_2$ |
| 3-CH$_2$CH=CH$_2$ |
| 4-CH$_2$CH=CH$_2$ |
| 2-C(CH$_3$)=CH$_2$ |
| 3-C(CH$_3$)=CH$_2$ |
| 4-C(CH$_3$)=CH$_2$ |
| 2-F-4-Cl-6-Br |
| 2,3,5,6-4F-4-CF$_3$ |
| 5-CF$_3$-2-OCH$_3$ |
| 4-CN-2,6-2Cl |
| 4-CF$_3$-2,6-2Cl |
| 4-CF$_3$-2,6-2Br |
| 2,3,4,5,6-5Cl |
| 5-CH$_3$-2-CONH$_2$ |
| 2-CH$_3$-5-CONH$_2$ |
| 2,3-2CH(CH$_3$)$_2$ |
| 2,4-2CH(CH$_3$)$_2$ |
| 2,5-2CH(CH$_3$)$_2$ |
| 2,6-2CH(CH$_3$)$_2$ |
| 4-NO$_2$-2,6-2Cl |
| 2,4-2NO$_2$-6-Cl |
| 2,4-2NO$_2$-6-Br |
| 3,4-2CH(CH$_3$)$_2$ |
| 3,5-2CH(CH$_3$)$_2$ |
| 2-NO$_2$-4-OCH$_3$ |
| 2-NO$_2$-4-OC$_2$H$_5$ |
| 4-CH$_3$-2,6-2Br |
| 5-CH$_3$-4-F-6-Cl |
| 4-C(CH$_3$)$_3$-2-Cl |
| 4-CF$_3$-2-Cl-6-Br |
| 2-CO$_2$CH$_3$-4-Br |
| 4-CO$_2$CH$_3$-2-Cl |
| 4-CO$_2$CH$_3$-2-Br |
| 2,4,6-3CH(CH$_3$)$_2$ |
| 2,4,6-3C(CH$_3$)$_2$ |
| 2,3-2CH$_3$-6-NO$_2$ |
| 2,4-2OCH$_3$-5-Cl |
| 2-OCH$_2$C≡Cl |
| 4-N(CH$_3$)$_2$-2-NO$_2$ |
| 5-N(CH$_3$)$_2$-2-NO$_2$ |
| 4,5-2CH$_3$-2-NO$_2$ |
| 2-NO$_2$-4-F-5-Cl |
| 2-CN-4-NO$_2$-6-Cl |
| 2-CN-4-NO$_2$-6-Br |
| 2-OCH$_2$CH=CH$_2$ |
| 3-OCH$_2$CH=CH$_2$ |
| 4-OCH$_2$CH=CH$_2$ |
| 2-OCH$_2$C≡CH |
| 3-OCH$_2$C≡CH |
| 4-OCH$_2$C≡CH |
| 5-NO$_2$-2-OCH$_3$ |
| 5-CH$_3$-2-OCH$_3$ |
| 4-COCH$_3$-2,6-2Cl |
| 4-OCF$_3$-2-NO$_2$ |
| 6-NO$_2$-2,3,4-3F |
| 4-NO$_2$-2,6-2Br |
| 4-NO$_2$-2,5-2Cl |
| 4-F-3-Cl-2,6-2Br |
| 2,3-(OCF$_2$O—) |
| 2,3-(OCH$_2$O—) |
| 3,4-(OCH$_2$O—) |
| 3,4-(OCF$_2$O—) |
| 3-CH$_3$-4-NHCOCH$_3$ |
| 4-CH$_3$-3-NHSO$_2$CH$_3$ |

TABLE 4-continued

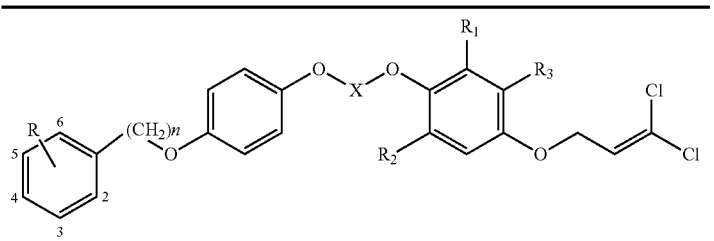

| R |
|---|
| 5-CH$_3$-2-OCH$_3$-4-Cl |
| 5-CF$_3$-2-NHCOCH$_3$ |
| 2-CH$_3$-4-NO$_2$-6-Cl |
| 2-CH$_3$-4-NO$_2$-6-Br |
| 2-CH$_3$-6-NO$_2$-4-Cl |
| 2-CH$_3$-6-NO$_2$-4-Br |
| 2,5-2OCH$_3$-4-NO$_2$ |
| 2,6-2CH$_3$-4-C(CH$_3$)$_3$ |
| 4-CF$_3$-2-NO$_2$-5-Cl |
| 4-CF$_3$-2-NO$_2$-6-Cl |
| 4-CF$_3$-2-NO$_2$-6-Br |
| 5-NHCOCH$_3$-2-Cl |
| 4-O(CH$_2$)$_2$N(CH$_3$)$_2$ |
| 2-CH$_2$C(CH$_3$)=CH$_2$ |
| 3-CH$_2$C(CH$_3$)=CH$_2$ |
| 4-CH$_2$C(CH$_3$)=CH$_2$ |
| 4-O(CH$_2$)$_3$CH$_3$-2-NO$_2$ |
| 3-OCH$_3$-4-CO$_2$CH$_3$ |
| 2-CH(CH$_3$)CH$_2$CH(CH$_3$)$_2$ |
| 2,3-(CH$_2$CH$_2$CH$_2$—) |
| 2,3-(CH$_2$CH$_2$CH$_2$CH$_2$—) |
| 2,3-(CH=CH—CH=CH—) |
| 4,5-(CH=CH—CH=CH—) |
| 2,3-(CCl=CH—CH=CH—) |
| 4,5-(CCl=CH—CH=CH—) |
| 2,3-(CH=CCl—CH=CH—) |
| 4,5-(CH=CCl—CH=CH—) |
| 2,3-(CH=CH—CCl=CH—) |
| 4,5-(CH=CH—CCl=CH—) |
| 2,3-(CH=NO$_2$—CH=CH—) |
| 4,5-(CH=NO$_2$—CH=CH—) |
| 2,3-(CH=CH—CH=CH—) |
| 4,5-(CH=CN—CH=CH—) |
| 2,3-(CH=CH$_3$—CH=CH—) |
| 6-Cl-2,3-(CH=CH—CH=CH—) |
| 6-Cl-2,3-(CCl=CH—CH=CH—) |
| 6-NO$_2$—2,3-(CH=CH—CH=CH—) |
| 6-NO$_2$-4,5-(CH=CH—CH=CH—) |
| 6-CN-2,3-(CH=CH—CH=CH—) |
| 6-CN-4,5-(CH=CH—CH=CH—) |

TABLE 5

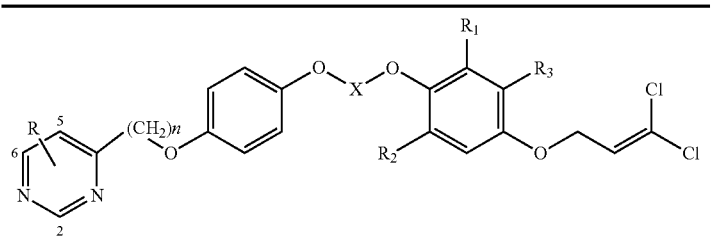

| R |
|---|
| 2-CH$_3$ |
| 2-Cl |
| 2-CN |
| 2-NH$_2$ |
| 2-C$_2$H$_5$ |
| 6-Cl |
| 6-OH |

TABLE 5-continued

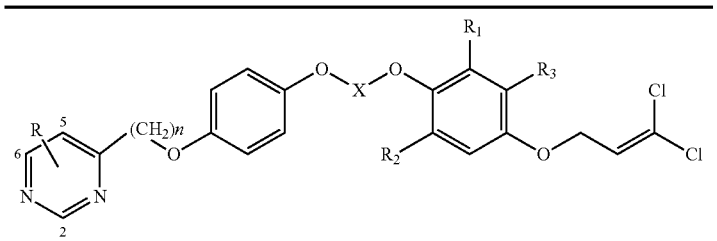

| R |
|---|
| 5-$CH_3$ |
| 5-Cl |
| 6-$C_2H_5$ |
| 5,6-2Cl |
| 6-$CHF_2$ |
| 6-$CF_3$ |
| 6-CN |
| 2-CN-6-Cl |
| 2-$CH_3$-6-Cl |
| 2-$CH_3$-6-OH |
| 2-$CH_3$-6-CN |
| 2-CN-6-$CF_3$ |
| 5-Cl-2-$NH_2$ |
| 2-$NH_2$-6-$CH_3$ |
| 2-$NH_2$-6-$CF_3$ |
| 2,6-2$NH_2$ |
| 2-NH2-6-Cl |
| 5-Cl-6-$CH_3$ |
| 6-$CHFCH_3$ |
| 6-$OCHF_2$ |
| 6-$OCH_3$ |
| 2-$CH_3$-6-$C_2H_5$ |
| 2-NH2-6-$OCH_3$ |
| 2-CN-6-$CH_3$ |
| 2-$SCH_3$-5-Br |
| 5-$NH_2$-6-Cl |
| 2-$SCH_3$-5-Cl |
| 2-$SCH_3$-6-Cl |
| 2-$SCH_3$-6-$CF_3$ |
| 2-$SCH_3$-6-$NH_2$ |
| 2-$SCH_3$-6-$CH_3$ |
| 5-Cl-6-$C_2H_5$ |
| 5,6-2Cl-2$NH_2$ |
| 5-Cl-6-$OCHF_2$ |
| 6-$OC(CH_3)_3$ |
| 2-$CH(CH_3)2$-6-Cl |
| 2-CN-5,6-2$CH_3$ |
| 2-$SO_2CH_3$-6-$CF_3$ |
| 2-$SO_2CH_3$-6-$CH_3$ |
| 2-$CF_3$-5,6-2$CH_3$ |
| 2-$CF_3$-5-$CO_2C_2H_5$ |
| 2-CN-5-$CH_3$-6-Cl |
| 2-$CONH_2$-6-$CH_3$ |
| 2-$CONH_2$-6-$CF_3$ |
| 2-$SCH_3$-5-OH-6-Cl |
| 5-Cl-6-$CF_3$ |
| 5-Cl-6-$CHFCH_3$ |
| 6-cyclopropyl |
| 5-Cl-6-$OCH_3$ |
| 2-(cyclopropyl)NH-6-$CF_3$ |
| 2-(cyclopropyl)-6-Cl |
| 2-(cyclopropyl)-6-$CH_3$ |
| 2-(cyclopropyl)-5-Cl-6-$CH_3$ |
| 2-(cyclopropyl)-5-Cl-6-$C_2H_5$ |
| 2-(cyclopropyl)-5,6-2Cl |
| 2-$CH_3$-5-Cl-6-$CF_3$ |
| 2-$CH_3$-5-Cl-6-$CH_3$ |
| 2-$CH_3$-5-Cl-6-$C_2H_5$ |
| 2-$CH_3$-5-Cl-6-$CHFCH_3$ |
| 2-$CH_3$-5-Cl-6-$CHF_2$ |
| 2-$CH_3$-5-Cl-6-$OCHF_2$ |
| 2-$CH_3$-5-Cl-6-$OCH_3$ |
| 5-Cl-6-CN |

TABLE 6
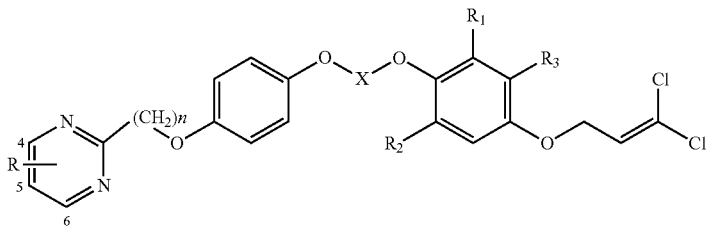
| R |
|---|
| 4-Cl |
| 4-CH₃ |
| 4-CF₃ |
| 4-C₂H₅ |
| 5-Cl |
| 5-Br |
| 4-CHF₂ |
| 4,6-2CH₃ |
| 4,6-2Cl |
| 4-Cl-5-Br |
| 4,5,6-3Cl |
| 4-CH₃-6-Cl |
| 4-CF₃-6-Cl |
| 4,5,6-3Cl |
| 4-CO₂CH₃ |
| 4,6-2OCH₃ |
| 5-CO₂CH₃ |
| 4-Cl-6-CH₃ |
| 5-CN |
| 4-CN |
| 4-OCH₃ |
| 4-NH₂-5-CN |
| 4-CHF₂-6-Cl |
| 4-CH₃-5,6-2Cl |
| 4-C₂H₅-5,6-2Cl |
| 4-CHF₂-5,6-Cl |
| 4-CH₃-6-CN |
| 4-OCH₃-6Cl |
| 4-CH₃-6-CO₂C₂H₅ |
| 4-CF₃-5-CO₂CH₃ |
| 4,5-(CH=CH—CH=CH—) |
| 4,5-(CH=CH—CH=CH—) |
| 4,5-(CH=CH—CH=CH-)-6-Cl |
| 4,5-(CH=CH—CCl=CH-)-6-Cl |
| 4,5-(C(CH₃)=CH—CH=CH-)-6-Cl |
TABLE 7
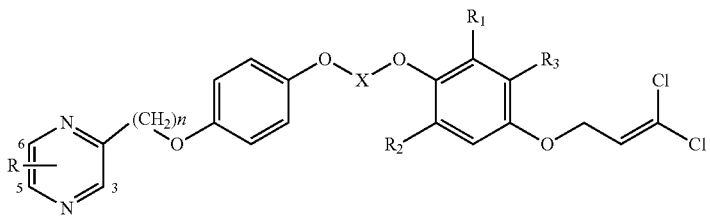
| R |
|---|
| 5-Br |
| 5-Cl |
| 5-CN |
| 6-Cl |
| 6-CN |
| 3-Cl |
| 3-Br |
| 5-CH₃ |
| 5-NH₂ |
| 5-SCH₃ |
| 6-SCH₃ |
| 5-OCH₃ |
| 6-OCH₃ |

TABLE 7-continued
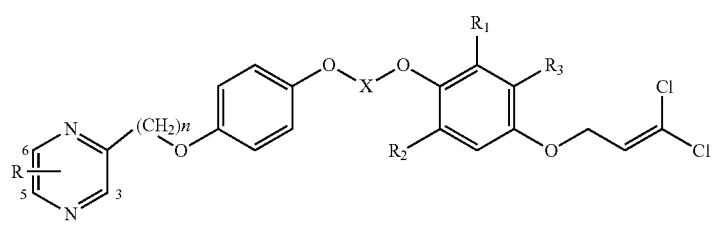
R
5,6-2CH$_3$
3-CH$_3$
3-CN
3-CF$_3$
3,5-2Cl
3-Cl-5-CH$_3$
3,5-2OCH$_3$
5-Cl-3-CN
5,6-(CH=CCl—CH=CH—)
5,6-(CH—CH—CH=CH—)
3-Cl-5,6-(CH=CH—CH=CH—)
5,6-(CCF$_3$=CH—CH=CH—)
5,6-(CCH$_3$=CH—CH=CH—)
5,6-(CCN=CH—CH=CH—)
4,5-(Cl=CH—CH=CH—)
TABLE 8
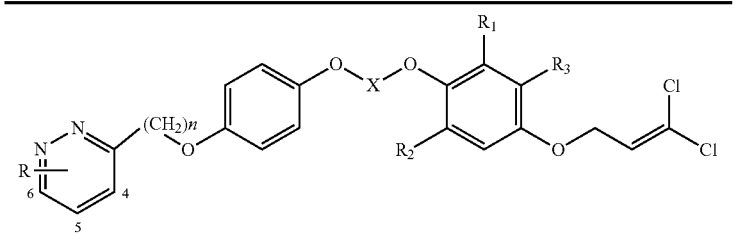
R
6-CN
6-Cl
6-CH$_3$
6-NH$_2$
6-Br
6-CF$_3$
6-SCH$_3$
6-OCH$_3$
4-NO$_2$
5-NO$_2$
4-CH$_3$-6-Cl
6-CH$_3$-4-Cl
6-NHCH$_3$
6-CHF$_2$
6-OCHF$_2$
6-OCH$_2$CF$_3$
6-OC(CH$_3$)$_3$
4-CN-6-Cl
4-NO$_2$-6-Cl
5-NO$_2$-6-Cl
4,5-(CH=CH—CH=CH—)
4,5-(CH=CH—CH=CH—)-6-Cl
4,5-(CH=CH—CH=CH—)-6-OCH$_3$
4,5-(CH=CCl—CH=CH—)-6-Cl
5,6-(CH=CH—CH=CH—)

TABLE 9

| R |
|---|
| 3-CHF$_2$ |
| 3-CH$_3$ |
| 3-CF$_3$ |
| 3-C$_2$H$_5$ |
| 4-NO$_2$ |
| 4-CN |
| 3-C(CH$_3$)$_3$ |
| 3,4-2CH$_3$ |
| 3-C$_2$H$_5$-4-Cl |
| 3-CH$_3$-4-Cl |
| 3-CH$_3$-4-Br |
| 3-CH$_3$-4-NO$_2$ |
| 3-CH$_3$-4-CN |
| 3-CH$_3$-4-CN |
| 3-CF$_3$-4-CH$_3$ |
| 3-CF$_3$-4-Cl |
| 3,4-(CH$_2$CH$_2$CH$_2$CH$_2$—) |
| 3,4-(CH=CH—CH=CH—) |
| 3,4-(CH=CCl—CH=CH—) |
| 3,4-(CH=CH—CCl=CH—) |

TABLE 10

| R |
|---|
| 3-CHF$_2$ |
| 3-CF$_3$-5-Cl |
| 3-CH$_3$-5-Cl |
| 3-NH$_2$ |
| 3,5-2CH$_3$ |
| 3-CH$_3$ |
| 5-CHF$_2$ |
| 5-Cl |
| 3-CF$_3$ |
| 3-CF$_3$-5-OCHF$_2$ |

TABLE 11

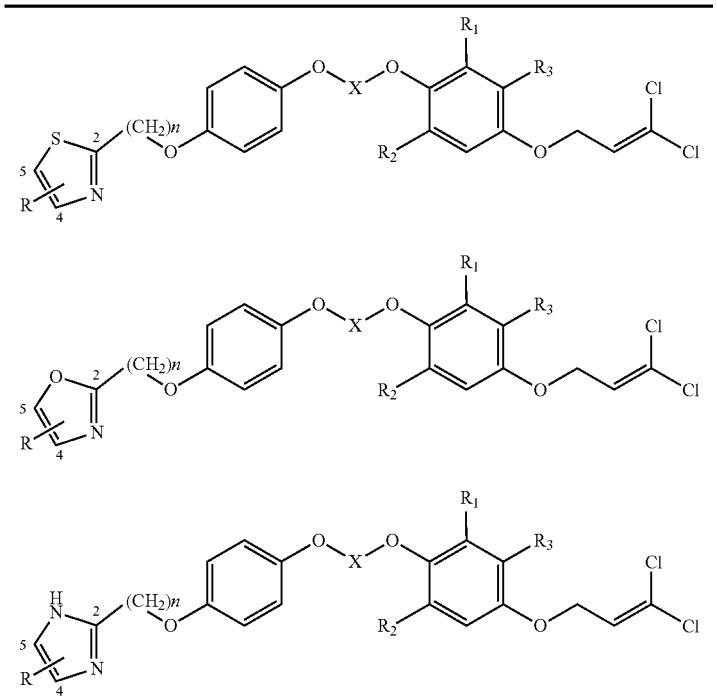

| R |
|---|
| 4-Br |
| 5-Cl |
| 5-CH$_3$ |
| 4-Cl |
| 5-Br |
| 4-CH$_3$ |
| 5-NO$_2$ |
| 5-OCH$_3$ |
| 4,5-2Cl |
| 4,5-2CH$_3$ |
| 4-C(CH$_3$)$_3$ |
| 4,5-(CH$_2$—)$_3$ |
| 4,5-(CH$_2$—)$_4$ |
| 4-CO$_2$C$_2$H$_5$ |
| 4-CF$_3$-5-CN |
| 4-CH$_2$CO$_2$C$_2$H$_5$ |
| 4-CH$_3$-5-COCH$_3$ |
| 4-CH$_3$-5-CO$_2$C$_2$H$_5$ |
| 4-CF$_3$-5-CO$_2$C$_2$H$_5$ |
| 5-CH$_3$-4-CO$_2$C$_2$H$_5$ |
| 4-CH$_3$-5-CONHCH$_3$ |
| 4-CF$_3$-5-CONHCH$_3$ |
| 4,5-(CH=CH—CH=CH—) |
| 4,5-(CCN=CH—CH=CH—) |
| 4,5-(CH=CBr—CH=CH—) |
| 4,5-(CCl=CH—CCl=CH—) |
| 4,5-(CH=CH—CBr=CH—) |
| 4,5-(CH=CH—CCN=CH—) |
| 4,5-(CCl=CH—CH=CH—) |
| 4,5-(CH=CCl—CH=CH—) |
| 4,5-(CH=CH—CCl=CH—) |
| 4,5-(CMe=CH—CH=CH—) |
| 4,5-(CH=CMe—CH=CH—) |
| 4,5-(C(OMe)=CH—CH=CH—) |
| 4,5-(CH=C(OMe)—CH=CH—) |
| 4,5-(CCF$_3$=CH—CH=CH—) |
| 4,5-(CNO$_2$=CH—CH=CH—) |
| 4,5-(CBr=CH—CH=CH—) |
| 4,5-(CH=CCN—CH=CH—) |
| 4,5-(CH=CCF$_3$—CH=CH—) |
| 4,5-(CH=CNO$_2$—CH=CH—) |
| 4,5-(CH=CH—CCF$_3$=CH—) |
| 4,5-(CH=CH—CNO$_2$=CH—) |
| 4,5-(CMe=CH—CCl=CH—) |

TABLE 11-continued

[Structure: thiazole-(CH2)n-phenyl-O-X-O-phenyl(R1,R2,R3)-O-CH2-CH=CCl2]

[Structure: oxazole-(CH2)n-phenyl-O-X-O-phenyl(R1,R2,R3)-O-CH2-CH=CCl2]

[Structure: imidazole-(CH2)n-phenyl-O-X-O-phenyl(R1,R2,R3)-O-CH2-CH=CCl2]

| R |
|---|
| 4,5-(CH=CMe—CCN=CH—) |
| 4,5-(CMe=CH—CNO$_2$=CH—) |
| 4,5-(CCl=CMe—CH=CH—) |
| 4,5-(CMe=CH—CNO$_2$=CH—) |
| 4,5-(CCN=CMe—CH=CH—) |
| 4,5-(CCF$_3$=CH—CCl=CH—) |
| 4,5-(CCN=CCF$_3$—CH=CH—) |
| 4,5-(CCF$_3$=CH—CCN=CH—) |
| 4,5-(CCl=CCF$_3$—CH=CH—) |
| 4,5-(CCN=CCl—CH=CH—) |

TABLE 12

[Structure: thiazole(5-position linkage)-(CH2)n-phenyl-O-X-O-phenyl(R1,R2,R3)-O-CH2-CH=CCl2]

| R |
|---|
| 2-CN |
| 2-Cl |
| 2-CH$_3$ |
| 2-Br |
| 2-NO$_2$ |
| 2-OCH$_3$ |
| 4-CH$_3$ |
| 2,4-2Cl |
| 4-CO$_2$C$_2$H$_5$ |
| 2,4-2CH$_3$ |
| 4-C(CH$_3$)$_3$ |
| 2-CN-4-CF$_3$ |
| 2-CF$_3$-4-CO$_2$C$_2$H$_5$ |
| 4-CH$_3$-2-COCH$_3$ |
| 4-CH$_3$-2-CO$_2$C$_2$H$_5$ |

TABLE 12-continued
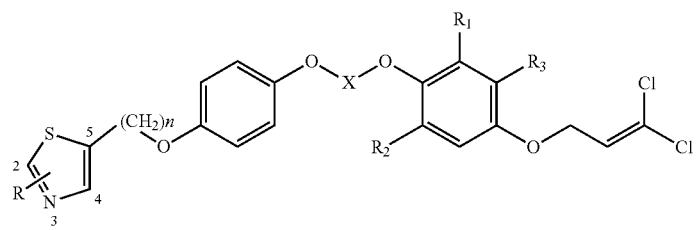
| R |
|---|
| 2-Ph |
| 4-CH$_3$-2-CONHCH$_3$ |
| 4-CF$_3$-2-CONHCH$_3$ |
| 2-CH$_3$-4-CO$_2$C$_2$H$_5$ |
| 2-(4-Cl—Ph) |
TABLE 13
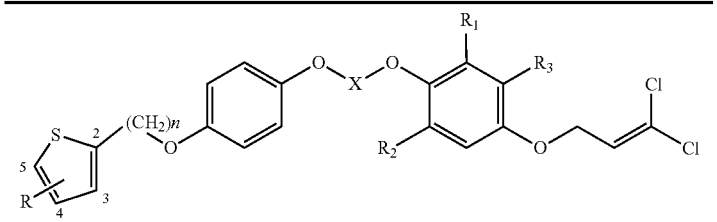
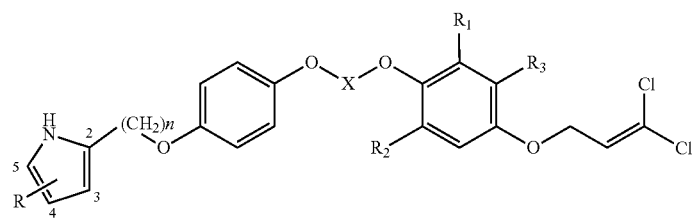
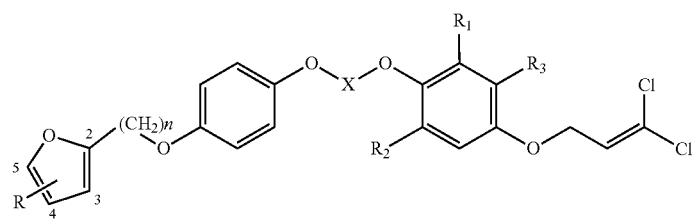
| R |
|---|
| 5-CN |
| 5-Cl |
| 5-CH$_3$ |
| 4-Cl |
| 3-Cl |
| 5-Br |
| 3-Br |
| 3-NO$_2$ |
| 4-CH$_3$ |
| 5-NO$_2$ |
| 3,4-2CH$_3$ |
| 5-OCH$_3$ |
| 4,5-2Cl |
| 3-CH$_3$ |
| 4,5-2CH$_3$ |
| 3-OCH$_3$ |
| 4-C(CH$_3$)$_3$ |
| 3,5-2CH$_3$ |
| 4-CO$_2$C$_2$H$_5$ |
| 3-COCH$_3$-4-CH$_3$ |

TABLE 13-continued
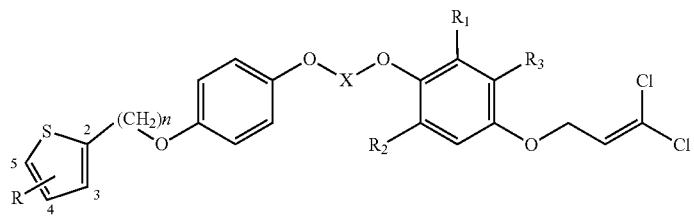
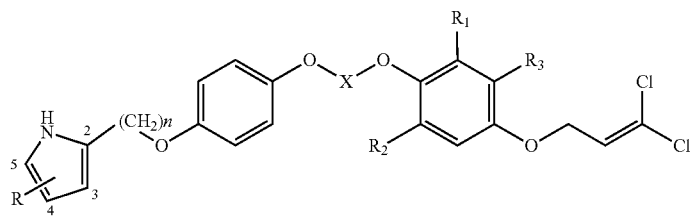
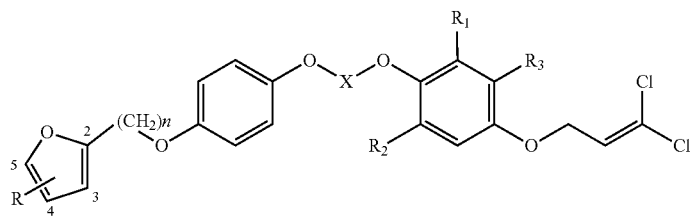
R
4,5-(CH$_2$—)$_3$
4,5-(CH$_2$—)$_4$
3-CO$_2$C$_2$H$_5$
4-CF$_3$-5-CN
4-CH$_2$CO$_2$C$_2$H$_5$
3-CH$_2$CO$_2$C$_2$H$_5$
3,4-(CH$_2$—)$_4$
4-CH$_3$-5-COCH$_3$
4-CH$_3$-5-CO$_2$C$_2$H$_5$
4-CF$_3$-5-CO$_2$C$_2$H$_5$
5-CH$_3$-4-CO$_2$C$_2$H$_5$
3-CF$_3$-5-CO$_2$C$_2$H$_5$
3-CO$_2$C$_2$H$_5$-4-CF$_3$
4-CH$_3$-5-CONHCH$_3$
4-CF$_3$-5-CONHCH$_3$
3-CF$_3$-5-CN
4,5-(CCl=CH—CH=CH—)
4,5-(CH=CCl—CH=CH—)
4,5-(CH=CH—CCl=CH—)
4,5-(CMe=CH—CH=CH—)
4,5-(CH=CMe—CH=CH—)
3,4-(CH=CH—CH=CH—)
4,5-(C(OMe)=CH—CH=CH—)
4,5-(CH=C(Ome)—CH=CH—)
4,5-(CH=CH—CH=CH—)

TABLE 14
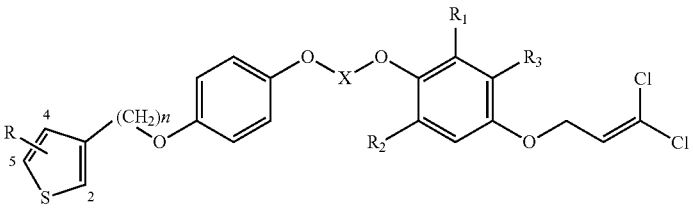
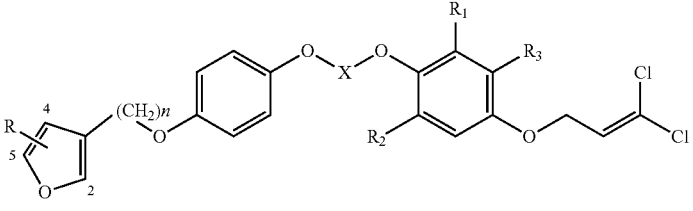
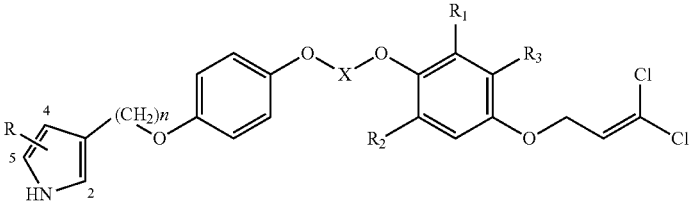
| R |
|---|
| 5-CN |
| 5-Cl |
| 5-CH$_3$ |
| 4-Cl |
| 2-Cl |
| 5-Br |
| 2-Br |
| 4-CH$_3$ |
| 5-NO$_2$ |
| 2-CH$_3$ |
| 2-NO$_2$ |
| 5-OCH$_3$ |
| 4,5-2Cl |
| 2,4-2Cl |
| 2,5-2Cl |
| 2,4-2CH$_3$ |
| 4-C(CH$_3$)$_3$ |
| 2-OCH$_3$ |
| 4-CF3 |
| 4-CN |
| 2-CN |
| 4-NO$_2$ |
| 4-CO$_2$C$_2$H$_5$ |
| 4-CH$_2$CO$_2$C$_2$H$_5$ |
| 2-CF$_3$-5-CN |
| 4,5-(CH$_2$—)$_4$ |
| 4-CF$_3$-5-CN |
| 4,5-(CH$_2$—)$_3$ |
| 2-CO$_2$C$_2$H$_5$ |
| 4,5-2CH$_3$ |
| 2,4-2CH$_3$ |
| 2,4-2Cl |
| 2,5-2CH$_3$ |
| 4-CH$_3$-5-COCH$_3$ |
| 4-CH$_3$-5-CO$_2$C$_2$H$_5$ |
| 4-CF$_3$-5-CO$_2$C$_2$H$_5$ |
| 5-CH$_3$-4-CO$_2$C$_2$H$_5$ |
| 2-COCH$_3$-4-CH$_3$ |
| 2-CF$_3$-5-CO$_2$C$_2$H$_5$ |
| 2-CO$_2$C$_2$H$_5$-4-CF$_3$ |
| 4-CF$_3$-5-CONHCH$_3$ |
| 2-CH$_3$-5-COCH$_3$ |
| 4-CH$_3$-5-CONHCH$_3$ |
| 2-Cl-4-NO$_2$ |
| 4,5-(CCl=CH—CH=CH—) |
| 4,5-(CH=CCl—CH=CH—) |

TABLE 14-continued
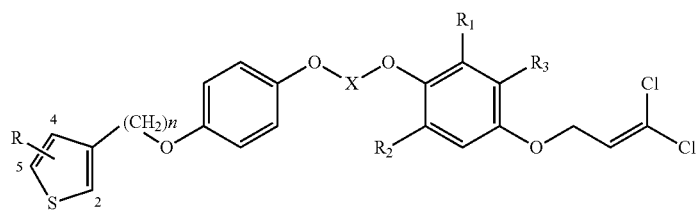
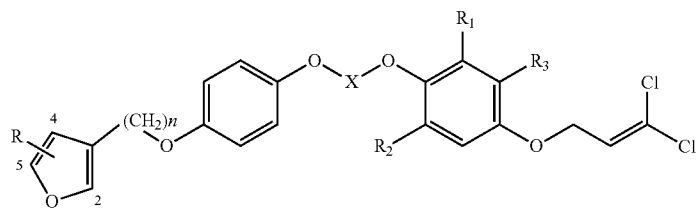
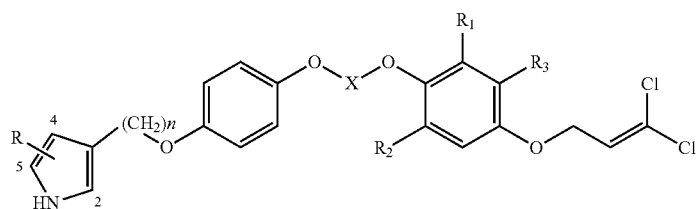
| R |
|---|
| 4,5-(CH=CH—CCl=CH—) |
| 4,5-(CH=CH—CH=CCl—) |
| 4,5-(Cme=CH—CH=CH—) |
| 4,5-(CH=Cme—CH=CH—) |
| 4,5-(C(Ome)=CH—CH=CH—) |
| 4,5-(CH=C(Ome)—CH=CH—) |
| 4,5-(CH=CH—CH=CH—) |
| 4,5-(C(NO$_2$)=CH—CH=CH—) |
| 4,5-(CH=C(NO$_2$)—CH=CH—) |
TABLE 15
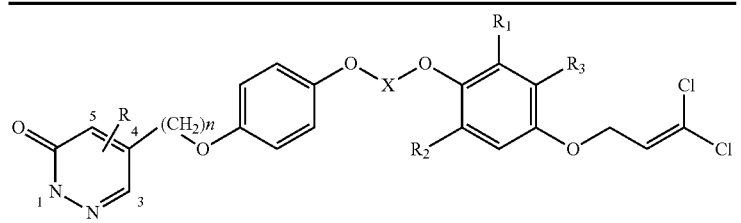
| R |
|---|
| 1-H-5-Cl |
| 1-C(CH$_3$)$_3$-5-Cl |
| 1-C$_2$H$_5$-5-Cl |
| 1-(4-Cl—Ph)-5-Cl |
| 1-CH$_3$-5-Cl |
| 1-CH$_3$-5-Br |
| 1-CH(CH$_3$)$_2$-5-Cl |
| 1-(4-Cl—Ph)-5-Br |
| 1-C(CH$_3$)$_3$-5-Br |
| 1-C(CH$_3$)$_3$-5-OCH$_3$ |
| 1-CO$_2$C$_2$H$_5$-5-Cl |
| 1-(4-NO$_2$—Ph)-5-Cl |

The present invention is also explained by the following compounds listed in Table 16, but without being restricted thereby.

TABLE 16

(I)

Structure: Q-O-(CH$_2$)$_n$-C$_6$H$_4$-O-X-O-C$_6$H$_2$(R$_1$)(R$_3$)(R$_2$)-O-CH$_2$-CH=CCl$_2$ with Cl substituent

| No. | Q | n | X | R$_1$ | R$_2$ | R$_3$ |
|---|---|---|---|---|---|---|
| 1 | 5-CF$_3$-pyridin-2-yl | 0 | —CH$_2$CH$_2$CH$_2$— | Cl | Cl | H |
| 2 | 3-Cl-5-CF$_3$-pyridin-2-yl | 0 | —CH$_2$CH$_2$CH$_2$— | Cl | Cl | H |
| 3 | 3-F-5-Cl-pyridin-2-yl | 0 | —CH$_2$CH$_2$CH$_2$— | Cl | Cl | H |
| 4 | 3,5-2Cl-2-pyridin-2-yl | 0 | —CH$_2$CH$_2$CH$_2$— | Cl | Cl | H |
| 5 | 3-Cl-5-CN-pyridin-2-yl | 0 | —CH$_2$CH$_2$CH$_2$— | Cl | Cl | H |
| 6 | 3-Cl-5-CCl$_3$-pyridin-2-yl | 0 | —CH$_2$CH$_2$CH$_2$— | Cl | Cl | H |
| 7 | 3-Cl-5-CH$_3$-pyridin-2-yl | 0 | —CH$_2$CH$_2$CH$_2$— | Cl | Cl | H |
| 8 | 3-Cl-pyridin-2-yl | 0 | —CH$_2$CH$_2$CH$_2$— | Cl | Cl | H |
| 9 | pyridin-2-yl | 0 | —CH$_2$CH$_2$CH$_2$— | Cl | Cl | H |
| 10 | 6-Cl-pyridin-2-yl | 0 | —CH$_2$CH$_2$CH$_2$— | Cl | Cl | H |
| 11 | 3,5,6-3Cl-pyridin-2-yl | 0 | —CH$_2$CH$_2$CH$_2$— | Cl | Cl | H |
| 12 | 3-CN-pyridin-2-yl | 0 | —CH$_2$CH$_2$CH$_2$— | Cl | Cl | H |
| 13 | 3-CN-4-CH$_3$-pyridin-2-yl | 0 | —CH$_2$CH$_2$CH$_2$— | Cl | Cl | H |
| 14 | 3-CN-4-CF$_3$-pyridin-2-yl | 0 | —CH$_2$CH$_2$CH$_2$— | Cl | Cl | H |
| 15 | 3-CN-4,6-2CH$_3$-pyridin-2-yl | 0 | —CH$_2$CH$_2$CH$_2$— | Cl | Cl | H |
| 16 | 6-CH$_3$-pyridin-2-yl | 0 | —CH$_2$CH$_2$CH$_2$— | Cl | Cl | H |
| 17 | 5-CH$_3$-pyridin-2-yl | 0 | —CH$_2$CH$_2$CH$_2$— | Cl | Cl | H |
| 18 | 4-CN-pyridin-2-yl | 0 | —CH$_2$CH$_2$CH$_2$— | Cl | Cl | H |
| 19 | 5-Cl-4-CN-pyridin-3-yl | 0 | —CH$_2$CH$_2$CH$_2$— | Cl | Cl | H |
| 20 | 4-CF$_3$-3-CN-6-Cl-pyridin-2-yl | 0 | —CH$_2$CH$_2$CH$_2$— | Cl | Cl | H |
| 21 | 2-Cl-3-CN-4-CF$_3$-pyridin-6-yl | 0 | —CH$_2$CH$_2$CH$_2$— | Cl | Cl | H |
| 22 | 4-CH$_3$-3-CN-6-Cl-pyridin-2-yl | 0 | —CH$_2$CH$_2$CH$_2$— | Cl | Cl | H |
| 23 | 2-Cl-3-CN-4-CH$_3$-pyridin-6-yl | 0 | —CH$_2$CH$_2$CH$_2$— | Cl | Cl | H |
| 24 | 3-CF$_3$-pyridin-2-yl | 0 | —CH$_2$CH$_2$CH$_2$— | Cl | Cl | H |
| 25 | 6-CF$_3$-3-Cl-pyridin-2-yl | 0 | —CH$_2$CH$_2$CH$_2$— | Cl | Cl | H |
| 26 | 2,3-2Cl-4-CF$_3$-pyridin-6-yl | 0 | —CH$_2$CH$_2$CH$_2$— | Cl | Cl | H |
| 27 | 6-CH$_3$-pyrimidin-4-yl | 0 | —CH$_2$CH$_2$CH$_2$— | Cl | Cl | H |
| 28 | 6-CF$_3$-pyrimidin-4-yl | 0 | —CH$_2$CH$_2$CH$_2$— | Cl | Cl | H |
| 29 | 6-CH$_3$-5-Cl-pyrimidin-4-yl | 0 | —CH$_2$CH$_2$CH$_2$— | Cl | Cl | H |
| 30 | 6-C$_2$H$_5$-5-Cl-pyrimidin-4-yl | 0 | —CH$_2$CH$_2$CH$_2$— | Cl | Cl | H |
| 31 | 6-CF$_3$-5-Cl-pyrimidin-4-yl | 0 | —CH$_2$CH$_2$CH$_2$— | Cl | Cl | H |
| 32 | 6-CH$_3$-5-Cl-2-CH$_3$-pyrimidin-4-yl | 0 | —CH$_2$CH$_2$CH$_2$— | Cl | Cl | H |
| 33 | 6-CH$_3$-2-Cl-pyrimidin-4-yl | 0 | —CH$_2$CH$_2$CH$_2$— | Cl | Cl | H |
| 34 | 6-CH$_3$-4-Cl-pyrimidin-2-yl | 0 | —CH$_2$CH$_2$CH$_2$— | Cl | Cl | H |
| 35 | 6-CH$_3$-2-SCH$_3$-pyrimidin-4-yl | 0 | —CH$_2$CH$_2$CH$_2$— | Cl | Cl | H |
| 36 | 3,5-2CH$_3$-pyrimidin-2-yl | 0 | —CH$_2$CH$_2$CH$_2$— | Cl | Cl | H |
| 37 | 3,5-OCH$_3$-pyrimidin-2-yl | 0 | —CH$_2$CH$_2$CH$_2$— | Cl | Cl | H |
| 38 | C$_6$H$_5$ | 0 | —CH$_2$CH$_2$CH$_2$— | Cl | Cl | H |
| 39 | 4-CF$_3$—C$_6$H$_4$ | 0 | —CH$_2$CH$_2$CH$_2$— | Cl | Cl | H |
| 40 | 2-Cl-4-CF$_3$—C$_6$H$_3$ | 0 | —CH$_2$CH$_2$CH$_2$— | Cl | Cl | H |
| 41 | 2,6-2Cl-4-CF$_3$—C$_6$H$_2$ | 0 | —CH$_2$CH$_2$CH$_2$— | Cl | Cl | H |
| 42 | 2-NO$_2$—C$_6$H$_4$ | 0 | —CH$_2$CH$_2$CH$_2$— | Cl | Cl | H |
| 43 | 4-NO$_2$—C$_6$H$_4$ | 0 | —CH$_2$CH$_2$CH$_2$— | Cl | Cl | H |
| 44 | 4-NO$_2$-3-CH$_3$—C$_6$H$_3$ | 0 | —CH$_2$CH$_2$CH$_2$— | Cl | Cl | H |
| 45 | 2-NO$_2$-4-CF$_3$—C$_6$H$_3$ | 0 | —CH$_2$CH$_2$CH$_2$— | Cl | Cl | H |
| 46 | 4-CN-2-F—C$_6$H$_3$ | 0 | —CH$_2$CH$_2$CH$_2$— | Cl | Cl | H |
| 47 | 5-Cl-benzoxazol-2-yl | 0 | —CH$_2$CH$_2$CH$_2$— | Cl | Cl | H |
| 48 | 5-CF$_3$-benzoxazol-2-yl | 0 | —CH$_2$CH$_2$CH$_2$— | Cl | Cl | H |
| 49 | 5-Cl-benzothiazol-2-yl | 0 | —CH$_2$CH$_2$CH$_2$— | Cl | Cl | H |
| 50 | 5-CF$_3$-benzothiazol-2-yl | 0 | —CH$_2$CH$_2$CH$_2$— | Cl | Cl | H |
| 51 | 6-Cl-quinoxalin-2-yl | 0 | —CH$_2$CH$_2$CH$_2$— | Cl | Cl | H |
| 52 | 6-Cl-pyridazin-3-yl | 0 | —CH$_2$CH$_2$CH$_2$— | Cl | Cl | H |
| 53 | 6-CH$_3$-pyridazin-3-yl | 0 | —CH$_2$CH$_2$CH$_2$— | Cl | Cl | H |
| 54 | 5-Cl-pyrazin-2-yl | 0 | —CH$_2$CH$_2$CH$_2$— | Cl | Cl | H |
| 55 | 6-Cl-pyrazin-2-yl | 0 | —CH$_2$CH$_2$CH$_2$— | Cl | Cl | H |
| 56 | 3-CF$_3$-pyrazol-5-yl | 0 | —CH$_2$CH$_2$CH$_2$— | Cl | Cl | H |
| 57 | 1-C(CH$_3$)$_3$-5-Cl-pyridazinone-4-yl | 0 | —CH$_2$CH$_2$CH$_2$— | Cl | Cl | H |
| 58 | 1-CH$_3$-5-Cl-pyridazinone-4-yl | 0 | —CH$_2$CH$_2$CH$_2$— | Cl | Cl | H |
| 59 | 1-CH$_3$-5-Br-pyridazinone-4-yl | 0 | —CH$_2$CH$_2$CH$_2$— | Cl | Cl | H |
| 60 | 1-C(CH$_3$)$_3$-5-Br-pyridazinone-4-yl | 0 | —CH$_2$CH$_2$CH$_2$— | Cl | Cl | H |
| 61 | 4-CF$_3$O—C$_6$H$_4$ | 1 | —CH$_2$CH$_2$CH$_2$— | Cl | Cl | H |
| 62 | 4-CF$_3$—C$_6$H$_4$ | 1 | —CH$_2$CH$_2$CH$_2$— | Cl | Cl | H |
| 63 | 4-C(CH$_3$)$_3$—C$_6$H$_4$ | 1 | —CH$_2$CH$_2$CH$_2$— | Cl | Cl | H |
| 64 | 4-CN—C$_6$H$_4$ | 1 | —CH$_2$CH$_2$CH$_2$— | Cl | Cl | H |

TABLE 16-continued (I)

| No. | Q | n | X | R$_1$ | R$_2$ | R$_3$ |
|---|---|---|---|---|---|---|
| 65 | 4-Cl—C$_6$H$_4$ | 1 | —CH$_2$CH$_2$CH$_2$— | Cl | Cl | H |
| 66 | 4-F—C$_6$H$_4$ | 1 | —CH$_2$CH$_2$CH$_2$— | Cl | Cl | H |
| 67 | 2-Cl—C$_6$H$_4$ | 1 | —CH$_2$CH$_2$CH$_2$— | Cl | Cl | H |
| 68 | 2-CH$_3$—C$_6$H$_4$ | 1 | —CH$_2$CH$_2$CH$_2$— | Cl | Cl | H |
| 69 | 2,4-2Cl—C$_6$H$_3$ | 1 | —CH$_2$CH$_2$CH$_2$— | Cl | Cl | H |
| 70 | 3,4-2Cl—C$_6$H$_3$ | 1 | —CH$_2$CH$_2$CH$_2$— | Cl | Cl | H |
| 71 | 2,6-2Cl—C$_6$H$_3$ | 1 | —CH$_2$CH$_2$CH$_2$— | Cl | Cl | H |
| 72 | 2-Cl-6-F—C$_6$H$_3$ | 1 | —CH$_2$CH$_2$CH$_2$— | Cl | Cl | H |
| 73 | 4-CH$_3$—C$_6$H$_4$ | 1 | —CH$_2$CH$_2$CH$_2$— | Cl | Cl | H |
| 74 | 4-CH$_3$O—C$_6$H$_4$ | 1 | —CH$_2$CH$_2$CH$_2$— | Cl | Cl | H |
| 75 | 2-CN—C$_6$H$_4$ | 1 | —CH$_2$CH$_2$CH$_2$— | Cl | Cl | H |
| 76 | 2-NO$_2$—C$_6$H$_4$ | 1 | —CH$_2$CH$_2$CH$_2$— | Cl | Cl | H |
| 77 | C$_6$H$_5$ | 1 | —CH$_2$CH$_2$CH$_2$— | Cl | Cl | H |
| 78 | 2-CF$_3$-pyridin-5-yl | 1 | —CH$_2$CH$_2$CH$_2$— | Cl | Cl | H |
| 79 | 2-Cl-pyridin-5-yl | 1 | —CH$_2$CH$_2$CH$_2$— | Cl | Cl | H |
| 80 | 2-Cl-thiazol-5-yl | 1 | —CH$_2$CH$_2$CH$_2$— | Cl | Cl | H |
| 81 | 5-Cl-indol-3-yl | 1 | —CH$_2$CH$_2$CH$_2$— | Cl | Cl | H |
| 82 | 5-F-indol-3-yl | 1 | —CH$_2$CH$_2$CH$_2$— | Cl | Cl | H |
| 83 | 5-CF$_3$-pyridin-2-yl | 0 | —CH$_2$CH$_2$CH$_2$— | Cl | H | H |
| 84 | 3-Cl-5-CF$_3$-pyridin-2-yl | 0 | —CH$_2$CH$_2$CH$_2$— | Cl | H | H |
| 85 | 3-F-5-Cl-pyridin-2-yl | 0 | —CH$_2$CH$_2$CH$_2$— | Cl | H | H |
| 86 | 3,5-2Cl-2-pyridin-2-yl | 0 | —CH$_2$CH$_2$CH$_2$— | Cl | H | H |
| 87 | 3-Cl-pyridin-2-yl | 0 | —CH$_2$CH$_2$CH$_2$— | Cl | H | H |
| 88 | 3,5,6-3Cl-pyridin-2-yl | 0 | —CH$_2$CH$_2$CH$_2$— | Cl | H | H |
| 89 | 3-CF$_3$-pyridin-2-yl | 0 | —CH$_2$CH$_2$CH$_2$— | Cl | H | H |
| 90 | 6-CH$_3$-5-Cl-pyrimidin-4-yl | 0 | —CH$_2$CH$_2$CH$_2$— | Cl | H | H |
| 91 | 6-C$_2$H$_5$-5-Cl-pyrimidin-4-yl | 0 | —CH$_2$CH$_2$CH$_2$— | Cl | H | H |
| 92 | 6-CF$_3$-5-Cl-pyrimidin-4-yl | 0 | —CH$_2$CH$_2$CH$_2$— | Cl | H | H |
| 93 | C$_6$H$_5$ | 0 | —CH$_2$CH$_2$CH$_2$— | Cl | H | H |
| 94 | 4-CF$_3$—C$_6$H$_4$ | 0 | —CH$_2$CH$_2$CH$_2$— | Cl | H | H |
| 95 | 2-Cl-4-CF$_3$—C$_6$H$_3$ | 0 | —CH$_2$CH$_2$CH$_2$— | Cl | H | H |
| 96 | 2,6-2Cl-4-CF$_3$—C$_6$H$_2$ | 0 | —CH$_2$CH$_2$CH$_2$— | Cl | H | H |
| 97 | 2-NO$_2$—C$_6$H$_4$ | 0 | —CH$_2$CH$_2$CH$_2$— | Cl | H | H |
| 98 | 4-NO$_2$—C$_6$H$_4$ | 0 | —CH$_2$CH$_2$CH$_2$— | Cl | H | H |
| 99 | 4-NO$_2$-3-CH$_3$—C$_6$H$_3$ | 0 | —CH$_2$CH$_2$CH$_2$— | Cl | H | H |
| 100 | 2-NO$_2$-4-CF$_3$—C$_6$H$_3$ | 0 | —CH$_2$CH$_2$CH$_2$— | Cl | H | H |
| 101 | 4-CN-2-F—C$_6$H$_3$ | 0 | —CH$_2$CH$_2$CH$_2$— | Cl | H | H |
| 102 | 5-Cl-benzoxazol-2-yl | 0 | —CH$_2$CH$_2$CH$_2$— | Cl | H | H |
| 103 | 5-CF$_3$-benzoxazol-2-yl | 0 | —CH$_2$CH$_2$CH$_2$— | Cl | H | H |
| 104 | 6-Cl-quinoxalin-2-yl | 0 | —CH$_2$CH$_2$CH$_2$— | Cl | H | H |
| 105 | 6-Cl-pyridazin-3-yl | 0 | —CH$_2$CH$_2$CH$_2$— | Cl | H | H |
| 106 | 1-C(CH$_3$)$_3$-5-Cl-pyridazinone-4-yl | 0 | —CH$_2$CH$_2$CH$_2$— | Cl | H | H |
| 107 | 4-C(CH$_3$)$_3$—C$_6$H$_4$ | 1 | —CH$_2$CH$_2$CH$_2$— | Cl | H | H |
| 108 | 4-CN—C$_6$H$_4$ | 1 | —CH$_2$CH$_2$CH$_2$— | Cl | H | H |
| 109 | 4-Cl—C$_6$H$_4$ | 1 | —CH$_2$CH$_2$CH$_2$— | Cl | H | H |
| 110 | 2,4-2Cl—C$_6$H$_3$ | 1 | —CH$_2$CH$_2$CH$_2$— | Cl | H | H |
| 111 | 2-Cl-6-F—C$_6$H$_3$ | 1 | —CH$_2$CH$_2$CH$_2$— | Cl | H | H |
| 112 | 2-CN—C$_6$H$_4$ | 1 | —CH$_2$CH$_2$CH$_2$— | Cl | H | H |
| 113 | 2-NO$_2$—C$_6$H$_4$ | 1 | —CH$_2$CH$_2$CH$_2$— | Cl | H | H |
| 114 | C$_6$H$_5$ | 1 | —CH$_2$CH$_2$CH$_2$— | Cl | H | H |
| 115 | 2-Cl-pyridin-5-yl | 1 | —CH$_2$CH$_2$CH$_2$— | Cl | H | H |
| 116 | 2-Cl-thiazol-5-yl | 1 | —CH$_2$CH$_2$CH$_2$— | Cl | H | H |
| 117 | 5-CF$_3$-pyridin-2-yl | 0 | —CH$_2$CH$_2$CH$_2$— | Cl | Cl | Cl |
| 118 | 3-Cl-5-CF$_3$-pyridin-2-yl | 0 | —CH$_2$CH$_2$CH$_2$— | Cl | Cl | Cl |
| 119 | 3-F-5-Cl-pyridin-2-yl | 0 | —CH$_2$CH$_2$CH$_2$— | Cl | Cl | Cl |
| 120 | 3,5-2Cl-2-pyridin-2-yl | 0 | —CH$_2$CH$_2$CH$_2$— | Cl | Cl | Cl |
| 121 | 3-Cl-pyridin-2-yl | 0 | —CH$_2$CH$_2$CH$_2$— | Cl | Cl | Cl |
| 122 | 3,5,6-3Cl-pyridin-2-yl | 0 | —CH$_2$CH$_2$CH$_2$— | Cl | Cl | Cl |
| 123 | 3-CF$_3$-pyridin-2-yl | 0 | —CH$_2$CH$_2$CH$_2$— | Cl | Cl | Cl |
| 124 | 6-CH$_3$-5-Cl-pyrimidin-4-yl | 0 | —CH$_2$CH$_2$CH$_2$— | Cl | Cl | Cl |
| 125 | 6-C$_2$H$_5$-5-Cl-pyrimidin-4-yl | 0 | —CH$_2$CH$_2$CH$_2$— | Cl | Cl | Cl |
| 126 | 6-CF$_3$-5-Cl-pyrimidin-4-yl | 0 | —CH$_2$CH$_2$CH$_2$— | Cl | Cl | Cl |
| 127 | C$_6$H$_5$ | 0 | —CH$_2$CH$_2$CH$_2$— | Cl | Cl | Cl |
| 128 | 4-CF$_3$—C$_6$H$_4$ | 0 | —CH$_2$CH$_2$CH$_2$— | Cl | Cl | Cl |
| 129 | 2-Cl-4-CF$_3$—C$_6$H$_3$ | 0 | —CH$_2$CH$_2$CH$_2$— | Cl | Cl | Cl |
| 130 | 2,6-2Cl-4-CF$_3$—C$_6$H$_2$ | 0 | —CH$_2$CH$_2$CH$_2$— | Cl | Cl | Cl |
| 131 | 2-NO$_2$—C$_6$H$_4$ | 0 | —CH$_2$CH$_2$CH$_2$— | Cl | Cl | Cl |
| 132 | 4-NO$_2$—C$_6$H$_4$ | 0 | —CH$_2$CH$_2$CH$_2$— | Cl | Cl | Cl |
| 133 | 4-NO$_2$-3-CH$_3$—C$_6$H$_3$ | 0 | —CH$_2$CH$_2$CH$_2$— | Cl | Cl | Cl |

TABLE 16-continued (I)

| No. | Q | n | X | R₁ | R₂ | R₃ |
|---|---|---|---|---|---|---|
| 134 | 2-NO₂-4-CF₃—C₆H₃ | 0 | —CH₂CH₂CH₂— | Cl | Cl | Cl |
| 135 | 4-CN-2-F—C₆H₃ | 0 | —CH₂CH₂CH₂— | Cl | Cl | Cl |
| 136 | 5-Cl-benzoxazol-2-yl | 0 | —CH₂CH₂CH₂— | Cl | Cl | Cl |
| 137 | 5-CF₃-benzoxazol-2-yl | 0 | —CH₂CH₂CH₂— | Cl | Cl | Cl |
| 138 | 6-Cl-quinoxalin-2-yl | 0 | —CH₂CH₂CH₂— | Cl | Cl | Cl |
| 139 | 6-Cl-pyridazin-3-yl | 0 | —CH₂CH₂CH₂— | Cl | Cl | Cl |
| 140 | 1-C(CH₃)₃-5-Cl-pyridazinone-4-yl | 0 | —CH₂CH₂CH₂— | Cl | Cl | Cl |
| 141 | 4-C(CH₃)₃—C₆H₄ | 1 | —CH₂CH₂CH₂— | Cl | Cl | Cl |
| 142 | 4-CN—C₆H₄ | 1 | —CH₂CH₂CH₂— | Cl | Cl | Cl |
| 143 | 4-Cl—C₆H₄ | 1 | —CH₂CH₂CH₂— | Cl | Cl | Cl |
| 144 | 2,4-2Cl—C₆H₃ | 1 | —CH₂CH₂CH₂— | Cl | Cl | Cl |
| 145 | 2-Cl-6-F—C₆H₃ | 1 | —CH₂CH₂CH₂— | Cl | Cl | Cl |
| 146 | 2-CN—C₆H₄ | 1 | —CH₂CH₂CH₂— | Cl | Cl | Cl |
| 147 | 2-NO₂—C₆H₄ | 1 | —CH₂CH₂CH₂— | Cl | Cl | Cl |
| 148 | C₆H₅ | 1 | —CH₂CH₂CH₂— | Cl | Cl | Cl |
| 149 | 2-Cl-pyridin-5-yl | 1 | —CH₂CH₂CH₂— | Cl | Cl | Cl |
| 150 | 2-Cl-thiazol-5-yl | 1 | —CH₂CH₂CH₂— | Cl | Cl | Cl |
| 151 | 2-CF₃-pyridin-2-yl | 0 | —CH₂CH₂— | Cl | Cl | H |
| 152 | 3-Cl-5-CF₃-pyridin-2-yl | 0 | —CH₂CH₂— | Cl | Cl | H |
| 153 | 3-F-5-Cl-pyridin-2-yl | 0 | —CH₂CH₂— | Cl | Cl | H |
| 154 | 3,5-2Cl-pyridin-2-yl | 0 | —CH₂CH₂— | Cl | Cl | H |
| 155 | 3-Cl-pyridin-2-yl | 0 | —CH₂CH₂— | Cl | Cl | H |
| 156 | 3,5,6-3Cl-pyridin-2-yl | 0 | —CH₂CH₂— | Cl | Cl | H |
| 157 | 3-CF₃-pyridin-2-y | 0 | —CH₂CH₂— | Cl | Cl | H |
| 158 | 6-CH₃-5-Cl-pyrimidin-4-yl | 0 | —CH₂CH₂— | Cl | Cl | H |
| 159 | 6-C₂H₅-5-Cl-pyrimidin-4-yl | 0 | —CH₂CH₂— | Cl | Cl | H |
| 160 | 6-CF₃-5-Cl-pyrimidin-4-yl | 0 | —CH₂CH₂— | Cl | Cl | H |
| 161 | C₆H₅ | 0 | —CH₂CH₂— | Cl | Cl | H |
| 162 | 4-CF₃—C₆H₄ | 0 | —CH₂CH₂— | Cl | Cl | H |
| 163 | 2-Cl-4-CF₃—C₆H₃ | 0 | —CH₂CH₂— | Cl | Cl | H |
| 164 | 2,6-2Cl-4-CF₃—C₆H₂ | 0 | —CH₂CH₂— | Cl | Cl | H |
| 165 | 2-NO₂—C₆H₄ | 0 | —CH₂CH₂— | Cl | Cl | H |
| 166 | 4-NO₂—C₆H₄ | 0 | —CH₂CH₂— | Cl | Cl | H |
| 167 | 4-NO₂-3-CH₃—C₆H₃ | 0 | —CH₂CH₂— | Cl | Cl | H |
| 168 | 2-NO₂-4-CF₃—C₆H₃ | 0 | —CH₂CH₂— | Cl | Cl | H |
| 169 | 4-CN-2-F—C₆H₃ | 0 | —CH₂CH₂— | Cl | Cl | H |
| 170 | 5-Cl-benzoxazol-2-yl | 0 | —CH₂CH₂— | Cl | Cl | H |
| 171 | 5-CF₃-benzoxazol-2-yl | 0 | —CH₂CH₂— | Cl | Cl | H |
| 172 | 6-Cl-quinoxalin-2-l | 0 | —CH₂CH₂— | Cl | Cl | H |
| 173 | 6-Cl-pyridazin-3-yl | 0 | —CH₂CH₂— | Cl | Cl | H |
| 174 | 1-C(CH₃)₃-5-Cl-pyridazinone-4-yl | 0 | —CH₂CH₂— | Cl | Cl | H |
| 175 | 4-C(CH₃)₃—C₆H₄ | 1 | —CH₂CH₂— | Cl | Cl | H |
| 176 | 4-CN—C₆H₄ | 1 | —CH₂CH₂— | Cl | Cl | H |
| 177 | 4-Cl—C₆H₄ | 1 | —CH₂CH₂— | Cl | Cl | H |
| 178 | 2,4-2Cl—C₆H₃ | 1 | —CH₂CH₂— | Cl | Cl | H |
| 179 | 2-Cl-6-F—C₆H₃ | 1 | —CH₂CH₂— | Cl | Cl | H |
| 180 | 2-CN—C₆H₄ | 1 | —CH₂CH₂— | Cl | Cl | H |
| 181 | 2-NO₂—C₆H₄ | 1 | —CH₂CH₂— | Cl | Cl | H |
| 182 | C₆H₅ | 1 | —CH₂CH₂— | Cl | Cl | H |
| 183 | 2-Cl-pyridin-5-yl | 1 | —CH₂CH₂— | Cl | Cl | H |
| 184 | 2-Cl-thiazol-5-yl | 1 | —CH₂CH₂— | Cl | Cl | H |
| 185 | 5-CF₃-pyridin-2-yl | 0 | —CH₂(CH₂)₂CH₂— | Cl | Cl | H |
| 186 | 3-Cl-5-CF₃-pyridin-2-yl | 0 | —CH₂(CH₂)₂CH₂— | Cl | Cl | H |
| 187 | 3-F-5-Cl-pyridin-2-yl | 0 | —CH₂(CH₂)₂CH₂— | Cl | Cl | H |
| 188 | 3,5-2Cl-pyridin-2-yl | 0 | —CH₂(CH₂)₂CH₂— | Cl | Cl | H |
| 189 | 3-Cl-pyridin-2-yl | 0 | —CH₂(CH₂)₂CH₂— | Cl | Cl | H |
| 190 | 3,5,6-3Cl-pyridin-2-yl | 0 | —CH₂(CH₂)₂CH₂— | Cl | Cl | H |
| 191 | 3-CF₃-pyridin-2-yl | 0 | —CH₂(CH₂)₂CH₂— | Cl | Cl | H |
| 192 | 6-CH₃-5-Cl-pyrimidin-4-yl | 0 | —CH₂(CH₂)₂CH₂— | Cl | Cl | H |
| 193 | 6-C₂H₅-5-Cl-pyrimidin-4-yl | 0 | —CH₂(CH₂)₂CH₂— | Cl | Cl | H |
| 194 | 6-CF₃-5-Cl-pyrimidin-4-yl | 0 | —CH₂(CH₂)₂CH₂— | Cl | Cl | H |
| 195 | C₆H₅ | 0 | —CH₂(CH₂)₂CH₂— | Cl | Cl | H |
| 196 | 4-CF₃—C₆H₄ | 0 | —CH₂(CH₂)₂CH₂— | Cl | Cl | H |

TABLE 16-continued (I)

$$\text{Q-(CH}_2)_n\text{-C}_6\text{H}_4\text{-O-X-O-C}_6\text{H}_2(R_1)(R_2)(R_3)\text{-O-CH}_2\text{-CH=CCl}_2$$

| No. | Q | n | X | $R_1$ | $R_2$ | $R_3$ |
|---|---|---|---|---|---|---|
| 197 | 2-Cl-4-CF$_3$—C$_6$H$_3$ | 0 | —CH$_2$(CH$_2$)$_2$CH$_2$— | Cl | Cl | H |
| 198 | 2,6-2Cl-4-CF$_3$—C$_6$H$_2$ | 0 | —CH$_2$(CH$_2$)$_2$CH$_2$— | Cl | Cl | H |
| 199 | 2-NO$_2$—C$_6$H$_4$ | 0 | —CH$_2$(CH$_2$)$_2$CH$_2$— | Cl | Cl | H |
| 200 | 4-NO$_2$—C$_6$H$_4$ | 0 | —CH$_2$(CH$_2$)$_2$CH$_2$— | Cl | Cl | H |
| 201 | 4-NO$_2$-3-CH$_3$—C$_6$H$_3$ | 0 | —CH$_2$(CH$_2$)$_2$CH$_2$— | Cl | Cl | H |
| 202 | 2-NO$_2$-4-CF$_3$—C$_6$H$_3$ | 0 | —CH$_2$(CH$_2$)$_2$CH$_2$— | Cl | Cl | H |
| 203 | 4-CN-2-F—C$_6$H$_3$ | 0 | —CH$_2$(CH$_2$)$_2$CH$_2$— | Cl | Cl | H |
| 204 | 5-Cl-benzoxazol-2-yl | 0 | —CH$_2$(CH$_2$)$_2$CH$_2$— | Cl | Cl | H |
| 205 | 5-CF$_3$-benzoxazol-2-yl | 0 | —CH$_2$(CH$_2$)$_2$CH$_2$— | Cl | Cl | H |
| 206 | 6-Cl-quinoxalin-2-yl | 0 | —CH$_2$(CH$_2$)$_2$CH$_2$— | Cl | Cl | H |
| 207 | 6-Cl-pyridazin-3-yl | 0 | —CH$_2$(CH$_2$)$_2$CH$_2$— | Cl | Cl | H |
| 208 | 1-C(CH$_3$)$_3$-5-Cl-pyridazinone-4-yl | 0 | —CH$_2$(CH$_2$)$_2$CH$_2$— | Cl | Cl | H |
| 209 | 4-C(CH$_3$)$_3$—C$_6$H$_4$ | 1 | —CH$_2$(CH$_2$)$_2$CH$_2$— | Cl | Cl | H |
| 210 | 4-CN—C$_6$H$_4$ | 1 | —CH$_2$(CH$_2$)$_2$CH$_2$— | Cl | Cl | H |
| 211 | 4-Cl—C$_6$H$_4$ | 1 | —CH$_2$(CH$_2$)$_2$CH$_2$— | Cl | Cl | H |
| 212 | 2,4-2Cl—C$_6$H$_3$ | 1 | —CH$_2$(CH$_2$)$_2$CH$_2$— | Cl | Cl | H |
| 213 | 2-Cl-6-F—C$_6$H$_3$ | 1 | —CH$_2$(CH$_2$)$_2$CH$_2$— | Cl | Cl | H |
| 214 | 2-CN—C$_6$H$_4$ | 1 | —CH$_2$(CH$_2$)$_2$CH$_2$— | Cl | Cl | H |
| 215 | 2-NO$_2$—C$_6$H$_4$ | 1 | —CH$_2$(CH$_2$)$_2$CH$_2$— | Cl | Cl | H |
| 216 | C$_6$H$_5$ | 1 | —CH$_2$(CH$_2$)$_2$CH$_2$— | Cl | Cl | H |
| 217 | 2-Cl-pyridin-5-yl | 1 | —CH$_2$(CH$_2$)$_2$CH$_2$— | Cl | Cl | H |
| 218 | 2-Cl-thiazol-5-yl | 1 | —CH$_2$(CH$_2$)$_2$CH$_2$— | Cl | Cl | H |
| 219 | 6-Cl-benzoxazol-2-yl | 0 | —CH$_2$CH$_2$CH$_2$— | Cl | Cl | H |
| 220 | 6-Cl-benzoxazol-2-yl | 0 | —CH$_2$CH$_2$CH$_2$— | Cl | H | H |
| 221 | 6-Cl-benzoxazol-2-yl | 0 | —CH$_2$CH$_2$CH$_2$— | Cl | Cl | Cl |
| 222 | 6-Cl-benzoxazol-2-yl | 0 | —CH$_2$CH$_2$— | Cl | Cl | H |
| 223 | 6-Cl-benzoxazol-2-yl | 0 | —CH$_2$(CH$_2$)$_2$CH$_2$— | Cl | Cl | H |
| 224 | 6-Cl-benzoxazol-2-yl | 0 | —CH$_2$CH$_2$CH$_2$— | H | H | H |
| 225 | 5-CF$_3$-pyridin-2-yl | 0 | —CH$_2$CH$_2$CH$_2$— | H | H | H |
| 226 | 3-Cl-5-CF$_3$-pyridin-2-yl | 0 | —CH$_2$CH$_2$CH$_2$— | H | H | H |
| 227 | 3-F-5-Cl-pyridin-2-yl | 0 | —CH$_2$CH$_2$CH$_2$— | H | H | H |
| 228 | 3,5-2Cl-pyridin-2-yl | 0 | —CH$_2$CH$_2$CH$_2$— | H | H | H |
| 229 | 3-Cl-pyridin-2-yl | 0 | —CH$_2$CH$_2$CH$_2$— | H | H | H |
| 230 | 3,5,6-3Cl-pyridin-2-yl | 0 | —CH$_2$CH$_2$CH$_2$— | H | H | H |
| 231 | 3-CF$_3$-pyridin-2-yl | 0 | —CH$_2$CH$_2$CH$_2$— | H | H | H |
| 232 | 6-CH$_3$-5-Cl-pyrimidin-4-yl | 0 | —CH$_2$CH$_2$CH$_2$— | H | H | H |
| 233 | 6-C$_2$H$_5$-5-Cl-pyrimidin-4-yl | 0 | —CH$_2$CH$_2$CH$_2$— | H | H | H |
| 234 | 6-CF$_3$-5-Cl-pyrimidin-4-yl | 0 | —CH$_2$CH$_2$CH$_2$— | H | H | H |
| 235 | C$_6$H$_5$ | 0 | —CH$_2$CH$_2$CH$_2$— | H | H | H |
| 236 | 4-CF$_3$—C$_6$H$_4$ | 0 | —CH$_2$CH$_2$CH$_2$— | H | H | H |
| 237 | 2-Cl-4-CF$_3$—C$_6$H$_3$ | 0 | —CH$_2$CH$_2$CH$_2$— | H | H | H |
| 238 | 2,6-2Cl-4-CF$_3$—C$_6$H$_2$ | 0 | —CH$_2$CH$_2$CH$_2$— | H | H | H |
| 239 | 2-NO$_2$—C$_6$H$_4$ | 0 | —CH$_2$CH$_2$CH$_2$— | H | H | H |
| 240 | 4-NO$_2$—C$_6$H$_4$ | 0 | —CH$_2$CH$_2$CH$_2$— | H | H | H |
| 241 | 4-NO$_2$-3-CH$_3$—C$_6$H$_3$ | 0 | —CH$_2$CH$_2$CH$_2$— | H | H | H |
| 242 | 2-NO$_2$-4-CH$_3$—C$_6$H$_3$ | 0 | —CH$_2$CH$_2$CH$_2$— | H | H | H |
| 243 | 4-CN-2-F—C$_6$H$_3$ | 0 | —CH$_2$CH$_2$CH$_2$— | H | H | H |
| 244 | 5-Cl-benzoxazol-2-yl | 0 | —CH$_2$CH$_2$CH$_2$— | H | H | H |
| 245 | 5-CF$_3$-benzoxazol-2-yl | 0 | —CH$_2$CH$_2$CH$_2$— | H | H | H |
| 246 | 6-Cl-quinoxalin-2-yl | 0 | —CH$_2$CH$_2$CH$_2$— | H | H | H |
| 247 | 6-Cl-pyridazin-3-yl | 0 | —CH$_2$CH$_2$CH$_2$— | H | H | H |
| 248 | 1-C(CH$_3$)$_3$-5-Cl-pyridazinone-4-yl | 0 | —CH$_2$CH$_2$CH$_2$— | H | H | H |
| 249 | 4-C(CH$_3$)$_3$—C$_6$H$_4$ | 1 | —CH$_2$CH$_2$CH$_2$— | H | H | H |
| 250 | 4-CN—C$_6$H$_4$ | 1 | —CH$_2$CH$_2$CH$_2$— | H | H | H |
| 251 | 4-Cl—C$_6$H$_4$ | 1 | —CH$_2$CH$_2$CH$_2$— | H | H | H |
| 252 | 2,4-2Cl—C$_6$H$_3$ | 1 | —CH$_2$CH$_2$CH$_2$— | H | H | H |
| 253 | 2-Cl-6-F—C$_6$H$_3$ | 1 | —CH$_2$CH$_2$CH$_2$— | H | H | H |
| 254 | 2-CN—C$_6$H$_4$ | 1 | —CH$_2$CH$_2$CH$_2$— | H | H | H |
| 255 | 2-NO$_2$—C$_6$H$_4$ | 1 | —CH$_2$CH$_2$CH$_2$— | H | H | H |
| 256 | C$_6$H$_5$ | 1 | —CH$_2$CH$_2$CH$_2$— | H | H | H |
| 257 | 2-Cl-pyridin-5-yl | 1 | —CH$_2$CH$_2$CH$_2$— | H | H | H |
| 258 | 2-Cl-thiazol-5-yl | 1 | —CH$_2$CH$_2$CH$_2$— | H | H | H |

The compounds having general formula (I) in present invention can be prepared according to the following method, each group of formulas is as defined above except special explanation.

The compounds having general formula (I) were prepared by reacting phenols having general formula (II) with dihalopropenyl intermediates (III) under basic conditions.

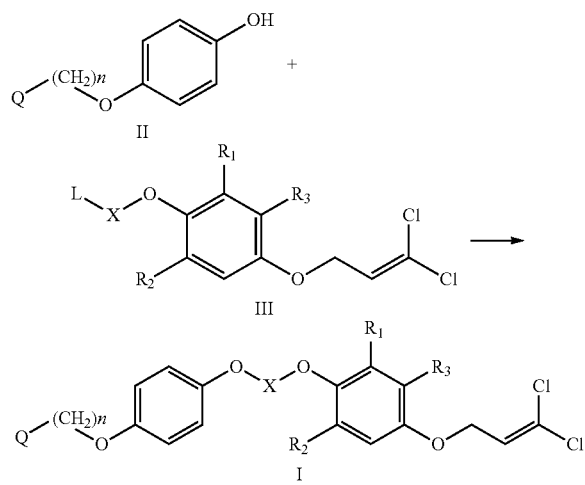

The compounds having general formula (II) were prepared by reacting compounds having general formula (IV) with p-dihydroxybenzene.

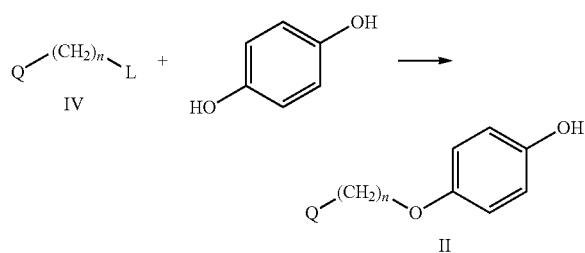

The compounds of the general formula (III) can be prepared according to the known methods, referring to CN1860874, US20030073847 and WO9727173 etc.

Some compounds of the general formula (IV) are commercially available, and can also be prepared according to the known methods, referring to U.S. Pat. No. 4,448,968, U.S. Pat. No. 4,528,379, EP0344684, US2006148867, JP2004346016, WO2009013195, JP2007091596, CN101056864, U.S. Pat. No. 5,240,940, WO2007088876, US2008280766, WO2009083105, WO2009068652, US2009105308, EP 2281812; J. Heterocyclic Chem., 2004, 41: 381; Arch. Pharm, Chem, Life Sci. 2005, 338: 117-125; J. Med, Chem, 1992, 35, 1299-1318.

The compounds of the general formula (III) and (IV), wherein L is leaving group selected from Cl or Br.

The reaction was carried out in proper solvent and the proper solvent mentioned may be selected from tetrahydrofuran, acetonitrile, toluene, xylene, benzene, N,N-dimethylformamide, dichloromethane, chloroform, acetone or butanone, and so on.

The proper base mentioned may be selected from potassium hydroxide, sodium hydroxide, sodium carbonate, potassium carbonate, sodium bicarbonate, triethylamine, pyridine, sodium hydride, potassium hydride, sodium amide, sodium methoxide, sodium ethoxide, sodium tert-butoxide or potassium tert-butoxide and so on.

The proper temperature mentioned is from room temperature to boiling point of solvent, normally the temperature is from 20 to 130° C.

The reaction time is in the range of 30 minutes to 20 hours, generally being 1-10 hours.

The compounds having general formula (I) have high insecticidal activity against adults, larvae and eggs of insects which are harmful in the agricultural, civil and zoo-technical field. Therefore, the present invention also includes the use of the compounds having general formula (I) as insecticides to control insect pests, both in agriculture and other fields.

In particular, the compounds having general formula (I) are active against important species of lepidopteran and diptera, such as striped rice borer (*Chilo suppressalis*), rice leaf roller (*Cnaphalocrocis medinalis*), diamond back moth (*Plutella xylostella*), beet armyworm (*Laphygma exigua*), armyworm (*Mythimna separata*), cotton leafworm (*Spodoptera litura*), housefly (*Musca domestica*) and so on, especially showed very good control of diamond back moth, armyworm, beet armyworm and housefly at very low doses. Therefore the compounds in the invention of general formula (I) can be used to control the pests of lepidoptera and diptera in agriculture and other fields.

Thanks to their positive characteristics, the compounds in the invention can be advantageously used in protecting crops of farming and gardening, domestic and breeding animals, as well as environments frequented by human beings, from harmful insects.

In order to obtain the desired effect, the dosage of compound to be applied can vary with various factors, for example, the used compound, the preserved crop, the type of harmful organism, the degree of infestation, the climatic conditions, the application method and the adopted formulation.

Doses of compound ranging from 10 g to 1000 g per hectare generally provide a sufficient control to the harmful insects.

Another object of the present invention also relates to a method for controlling insects in crops of farming and gardening and/or on domestic and breeding animals and/or environments frequented by human beings, by the application of the compounds having general formula W. In particular, the dosage of compound to be applied varies from 10 g to 1000 g per hectare.

For practical use in agriculture, it is usually useful to use compositions containing one or more compounds having general formula (I).

Therefore a technical object of the present invention relates to insecticidal compositions containing one or more compounds having general formula (I) as active ingredient and the weight percentage of the active ingredient in the composition is 0.1-99%.

Compositions can be used in the form of dry powders, wettable powders, emulsifiable concentrates, microemulsions, pastes, granulates, solutions, suspensions, etc.: the selection of the type of composition depends on the specific use.

The compositions are prepared in the known way, for example by diluting or dissolving the active substance with a solvent medium and/or a solid diluent, optionally in the presence of surface-active agents.

Solid diluents or carriers which can be used include, for example: silica, kaolin, bentonite, talc, diatomite, dolomite, calcium carbonate, magnesia, chalk, clays, synthetic silicates, attapulgite, seppiolite and so on.

Liquid diluents which can be used include, for example, in addition to water, aromatic organic solvents (xylols or mixtures of alkylbenzols, chlorobenzene, etc.), paraffins (petroleum fractions), alcohols (methanol, propanol, butanol, octanol, glycerin), esters (ethyl acetate, isobutyl acetate, etc.), ketones (cyclohexanone, acetone, acetophenone, isophorone, ethylainylketone, etc.), amides (N,N-dimethylformamide, N-methylpyrrolidone, etc.).

Surface-active agents which can be used include salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such as Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 0.5 to 90%, preferably from 5 to 60%.

If required, other active ingredients being compatible with the compounds having general formula (I) can be added to the compositions, such as, other acaricides/insecticides, fungicides, plant growth regulators, antibiotics, herbicides, fertilizers.

The preparation methods of several common formulations examples in the present invention are as follows:

The preparation of suspension concentrate: in commonly used for producing the suspension concentrate, the active component in formula is 5%-35%. With water as the medium, the compound in the invention, dispersing agent, suspending agent and antifreeze are added to sanding machine for grinding to make suspension concentrate.

The preparation of water emulsion: the compound in the invention, solvent and emulsifier are mixed together, to make a homogeneous oil phase. The water is mixed with antifreeze to make a homogeneous water phase. In the high-speed stirring, the aqueous phase is added to the oil phase or oil phase is added to the aqueous phase, forming the water emulsion with good dispersity. The active component of water emulsions is generally 5%-15% in this invention. For the production of concentrated emulsions, the compounds of this invention are dissolved in one or more of the mixed solvent, and then emulsifier was added to enhance dispersion effects in the water.

The preparation of wettable powder: according to formulation requirements, the compound in the invention, surfactants and solid diluents are mixed well, after smashing through ultrafine pulverizer, that is the wettable powder products (for example, 10%-60%). For the preparation of the spraying wettable powder, the compounds of this invention can be formed the mixture with solid powder, such as clay inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation certain mesh machine for granulation, then by drying and sieving (at the scope screen). Also, the compound in the invention, dispersants, disintegrants, wetting agents and solid diluent are added to sanding machine, grinding in water to produce suspension and then spray-drying granulation, usually the content of the prepared granular products is 20%-30%.

DESCRIPTION OF THE INVENTION IN DETAIL

The following examples are illustrative of the present invention, but without being restricted thereby. (All the starting materials are commercially available except special explanation).

PREPARATION EXAMPLE

Example 1

The Preparation of Compound 1

(1) The preparation of 4-(5-(trifluoromethyl)pyridin-2-yloxy)phenol

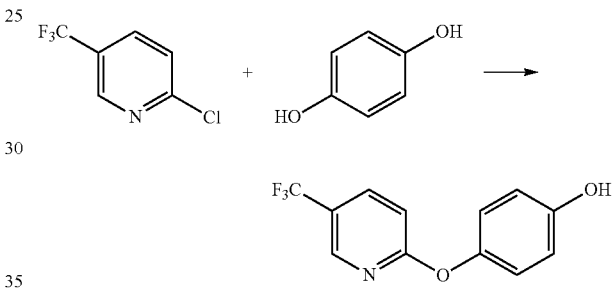

p-dihydroxybenzene 12.1 g (0.11 mol), anhydrous potassium carbonate 15.2 g (0.11 mol) were added to 500 mL of three-necked flask with DMF (200 mL) in sequence, the reaction mixture was then heated to 60° C., forming pale yellow turbid liquid, a solution of 2-chloro-5-(trifluoromethyl)pyridine 18.2 g (0.1 mol) in DMF (50 mL) was added dropwise to the above solution, after completion of addition for 15 min, then the mixture was heated to 90° C. and stirred for another 4 hours at this temperature. The reaction was monitored by thin-layer chromatography (TLC). After the reaction was completed, the reaction mixture was cooled to room temperature, then poured into water (300 mL) and extracted with ethyl acetate (2×300 mL). The organic phases were combined, washed with brine (2×200 mL), dried over anhydrous magnesium sulfate, concentrated under reduced pressure and the residue was purified via silica gel column chromatography (Fluent: ethyl acetate/petroleum ether=1:8) to give the product (19.1 g) as a white solid in 75% yield.

(2) The Preparation of Compound 1

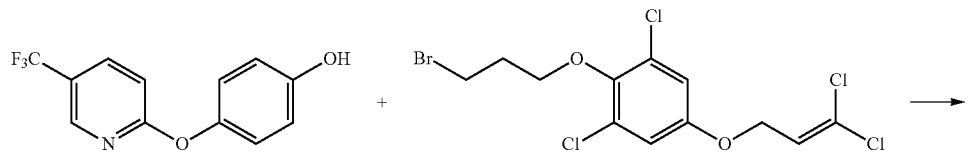

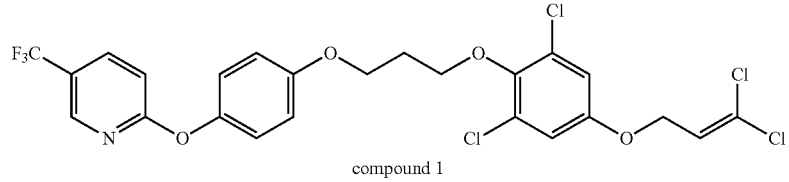

compound 1

4-(5-(trifluoromethyl)pyridin-2-yloxy)phenol 0.77 g (3 mmol), 2-(3-bromopropoxy)-1,3-dichloro-5-(3,3-dichloroallyloxy)benzene 1.23 g (3 mmol, prepared according to WO9604228A1), anhydrous potassium carbonate 0.62 g (4.5 mmol) were added to 100 mL of flask with acetonitrile (50 mL) in sequence, the reaction mixture was then heated to reflux for 1 h. The reaction was monitored by thin-layer chromatography (TLC). After the reaction was completed, the reaction mixture was cooled to room temperature, filtered, concentrated under reduced pressure and the residue was purified via silica gel column chromatography (Fluent: ethyl acetate/petroleum ether-1:30) to give the product (1.52 g) as colorless oil in 87% yield.

added dropwise to the above solution, after completion of addition for 15 min, then the mixture was refluxed for another 3 h. The reaction was monitored by thin-layer chromatography (TLC). After the reaction was completed, the reaction mixture was cooled to room temperature, filtered, concentrated under reduced pressure and the residue was purified via silica gel column chromatography (Fluent: ethyl acetate/petroleum ether-1:8) to give the product (24.9 g) as a white solid in 86% yield.

(2) The Preparation of Compound 2

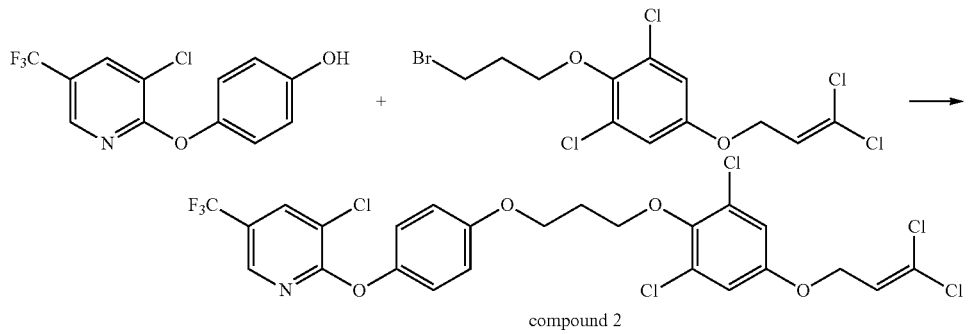

compound 2

$^1$H-NMR spectrum (300 MHz, internal standard TMS, solvent CDCl$_3$) is as follows: δppm 8.45 (s, 1H), 7.87 (d, 1H), 7.07 (d, 2H), 6.98 (d, 2H), 6.84 (m, 1H), 6.83 (s, 2H), 4.57 (d, 2H), 4.27 (t, 2H), 4.17 (t, 2H), 2.30 (m, 2H).

Example 2

The Preparation of Compound 2

(1) The preparation of 4-(3-chloro-5-(trifluoromethyl)pyridin-2-yloxy)phenol

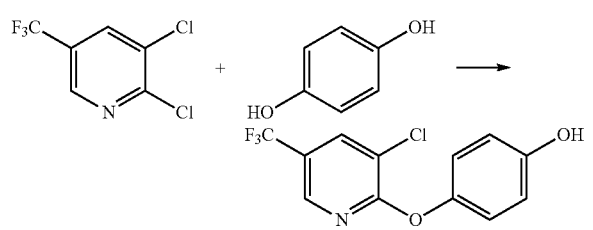

p-dihydroxybenzene 12.1 g (0.11 mol), anhydrous potassium carbonate 15.2 g (0.11 mol) were added to 500 mL of three-necked flask with 2-butanone (200 mL) in sequence, the reaction mixture was then heated to reflux, forming milky white turbid liquid, a solution of 2,3-dichloro-5-(trifluoromethyl)pyridine 21.6 g (0.1 mol) in 2-butanone (50 mL) was 4-(3-chloro-5-(trifluoromethyl)pyridin-2-yloxy)phenol 0.87 g (3 mmol), 2-(3-bromopropoxy)-1,3-dichloro-5-(3,3-dichloroallyloxy)benzene 123 g (3 mmol), anhydrous potassium carbonate 0.62 g (4.5 mmol) were added to 100 ad, of flask with acetonitrile (50 mL) in sequence, the reaction mixture was then heated to reflux for 2 h. The reaction was monitored by thin-layer chromatography (TLC). After the reaction was completed, the reaction mixture was cooled to room temperature, filtered, concentrated under reduced pressure and the residue was purified via silica gel column chromatography (Fluent: ethyl acetate/petroleum ether=1:30) to give the product (1.56 g) as pale yellow oil in 84% yield.

$^1$H-NMR spectrum (300 MHz, internal standard TMS, solvent CDCl$_3$) is as follows: δppm 8.27 (s, 1H), 7.96 (s, 1H), 7.10 (d, 2H), 6.98 (d, 2H), 6.84 (s, 2H), 6.11 (t, 1H), 4.58 (d, 2H), 4.28 (t, 2H), 4.17 (t, 2H), 231 (m, 2H).

Example 3

The Preparation of Compound 38

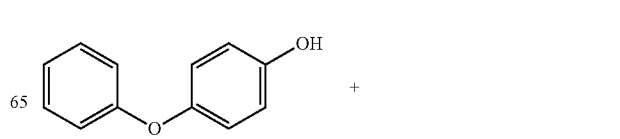

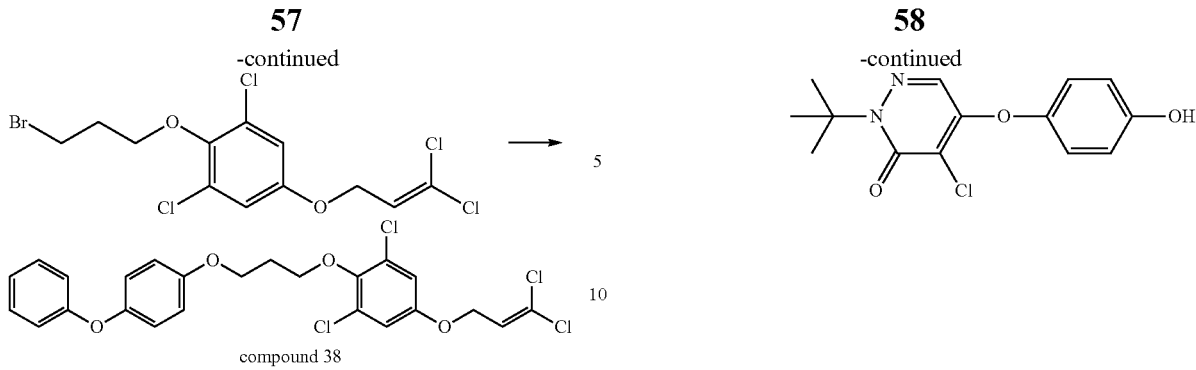

compound 38

4-phenoxyphenol 0.56 g (3 mmol), 2-(3-bromopropoxy)-1,3-dichloro-5-(3,3-dichloroallyloxy)benzene 123 g (3 mmol), anhydrous potassium carbonate 0.62 g (4.5 mmol) were added to 100 mL of flask with acetonitrile (50 mL) in sequence, the reaction mixture was then heated to reflux for 1 h. The reaction was monitored by thin-layer chromatography (TLC). After the reaction was completed, the reaction mixture was cooled to room temperature, filtered, concentrated under reduced pressure and the residue was purified via silica gel column chromatography (Fluent: ethyl acetate/petroleum ether=1:20) to give the product (1.22 g) as pale yellow oil in 79% yield.

The preparation process was the same as that in step (1) of example 2, only replacing 2,3-dichloro-5-(trifluoromethyl)pyridine with 2-tart-butyl-4,5-dichloropyridazin-3(2H)-one (22.1 g, 0.1 mol), the residue was purified via silica gel column chromatography (Fluent: ethyl acetate/petroleum ether-1:5) to give the product (21.2 g) as pale yellow solid in 72% yield.

(2) The Preparation of Compound 57

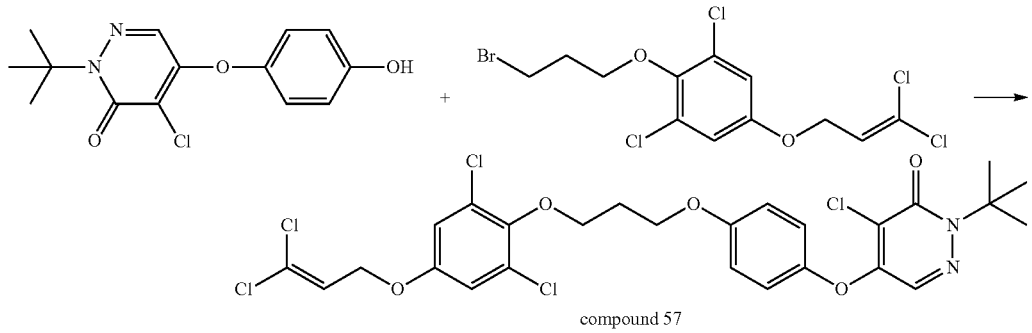

compound 57

¹H-NMR spectrum (300 MHz, internal standard TMS, solvent CDCl₃) is as follows: δppm 7.30 (m, 2H), 6.89-7.04 (m, 7H), 6.84 (s, 2H), 6.10 (t, 1H), 4.57 (d, 2H), 4.25 (t, 2H), 4.16 (t, 2H), 2.29 (m, 2H).

Example 4

The Preparation of Compound 57

(1) The preparation of 2-tort-butyl-4-chloro-5-(4-hydroxyphenoxy)pyridazin-3(2H)-one The preparation process was the same as that in step (2) of example L only replacing 4-(3-chloro-5-(trifluoromethyl)pyridin-2-yloxy)phenol with 2-tert-butyl-4-chloro-5-(4-hydroxyphenoxy)pyridazin-3(2H)-one (0.88 g, 3 mmol), the residue was purified via silica gel column chromatography (Fluent: ethyl acetate/petroleum ether=1:30) to give the product (1.25 g) as pale yellow oil in 68% yield.

¹H-NMR spectrum (300 MHz, internal standard TMS, solvent CDCl₃) is as follows: δppm 7.39 (s, 1H), 7.05 (d, 2H), 6.96 (d, 2H), 6.84 (s, 2H), 6.11 (t, 1H), 4.58 (d, 2H), 4.17 (t, 2H), 4.14 (t, 2H), 130 (m, 2H).

Example 5

The Preparation of Compound 72

(1) The preparation of 4-(2-chloro-6-fluorobenzyloxy)phenol

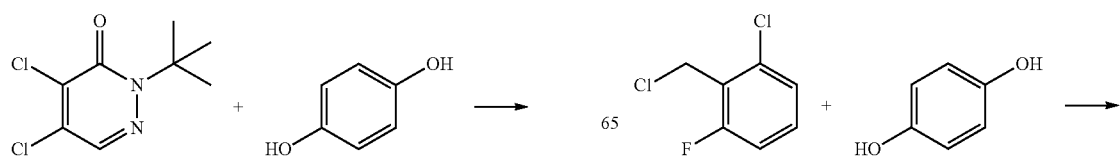

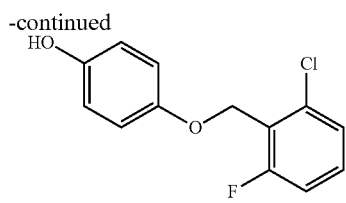

The preparation process was the same as that in step (1) of example 2, only replacing 2,3-dichloro-5-(trifluoromethyl) pyridine with 2-chloro-6-fluorobenzyl chloride (17.9 g, 0.1 mol), the residue was purified via silica gel column chromatography (Fluent: ethyl acetate/petroleum ether=10) to give the product (21.4 g) as white solid in 85% yield.

(2) The Preparation of Compound 72

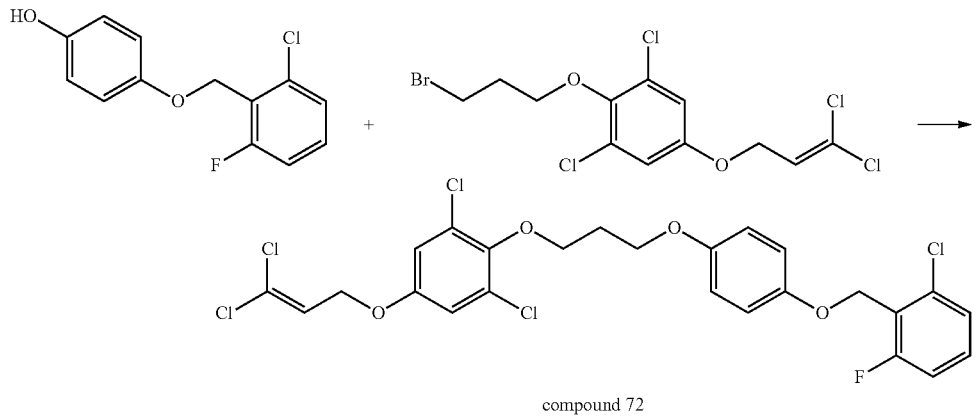

compound 72

The preparation process was the same as that in step (2) of example 1, only replacing 4-(3-chloro-5-(trifluoromethyl)pyridin-2-yloxy)phenol with 4-(2-chloro-6-fluorobenzyloxy)phenol (0.75 g, 3 mmol), the residue was purified via silica gel column chromatography (Fluent: ethyl acetate/petroleum ether=1:30) to give the product (1.40 g) as colorless oil in 81% yield.

$^1$H-NMR spectrum (300 MHz, internal standard TMS, solvent $CDCl_3$) is as follows: δppm 6.96 (m, 3H), 6.88 (m, 4H), 6.83 (s, 2H), 6.11 (t, 1H), 5.13 (s, 2H), 4.59 (d, 2H), 4.22 (t, 2H), 4.15 (t, 2H), 2.27 (m, 2H).

Example 6

The preparation of compound 80

(1) The preparation of 4-((2-chlorothiazol-5-yl)methoxy)phenol

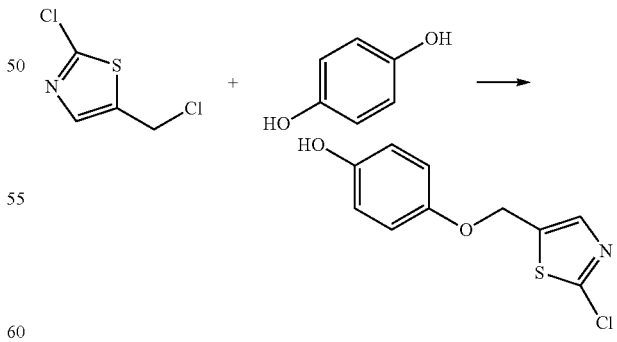

The preparation process was the same as that in step (1) of example 2, only replacing 2,3-dichloro-5-(trifluoromethyl) pyrid with 2-chloro-5-(chloromethyl)thiazole (16.8 g, 4.1 mol), the residue was purified via silica gel column chromatography (Fluent: ethyl acetate/petroleum ether=1:6) to give the product (17.8 g) as pale yellow solid in 74% yield.

(2) The Preparation of Compound 80

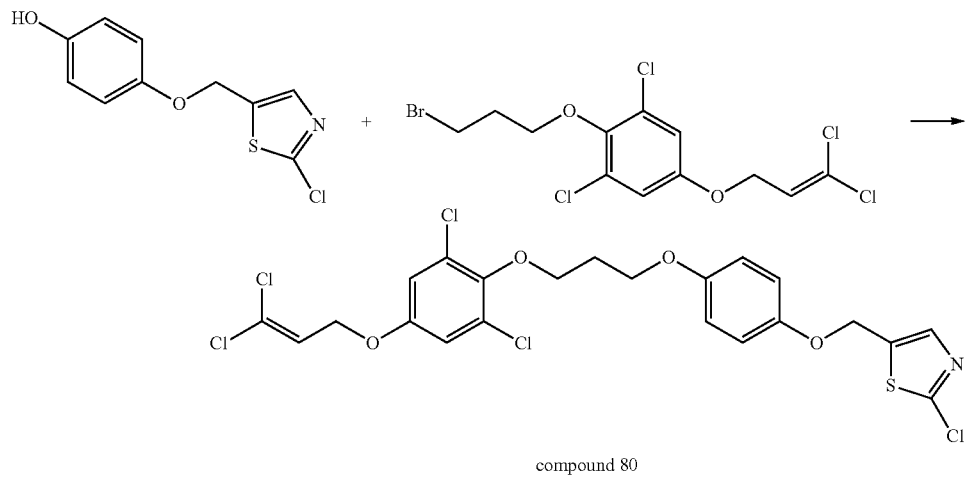

compound 80

The preparation process was the same as that in step (2) of example 1, only replacing 4-(3-chloro-5-(trifluoromethyl)pyridin-2-yloxy)phenol with 4-((2-chlorothiazol-5-yl)methoxy)phenol (0.72 g, 3 mmol), the residue was purified via silica gel column chromatography (Fluent: ethyl acetate/petroleum ether=1:30) to give the product (1.40 g) as pale yellow oil in 82% yield.

$^1$H-NMR spectrum (300 MHz, internal standard TMS, solvent CDCl$_3$) is as follows: δppm 7.59 (s, 1H), 6.86 (m, 4H), 6.84 (s, 2H), 6.11 (t, 1H), 5.12 (s, 2H), 4.58 (d, 2H), 4.20 (m, 4H), 2.27 (m, 2H).

Example 7

The Preparation of Compound 219

(1) The preparation of 4-(6-chlorobenzo[d]oxazol-2-yloxy)phenol

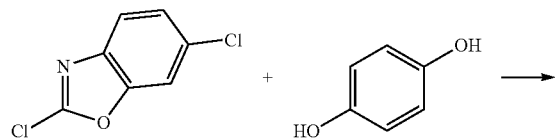

-continued

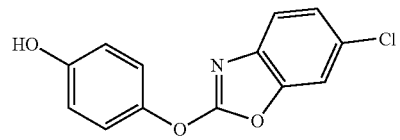

The preparation process was the same as that in step (1) of example 2, only replacing 2,3-dichloro-5-(trifluoromethyl)pyridine with 2,6-dichlorobenzo[d]oxazole (18.8 g, 0.1 mol), the residue was purified via silica gel column chromatography (Fluent: ethyl acetate/petroleum ether=1:10) to give the product (22.8 g) as gray solid in 87% yield.

(2) The Preparation of Compound 219

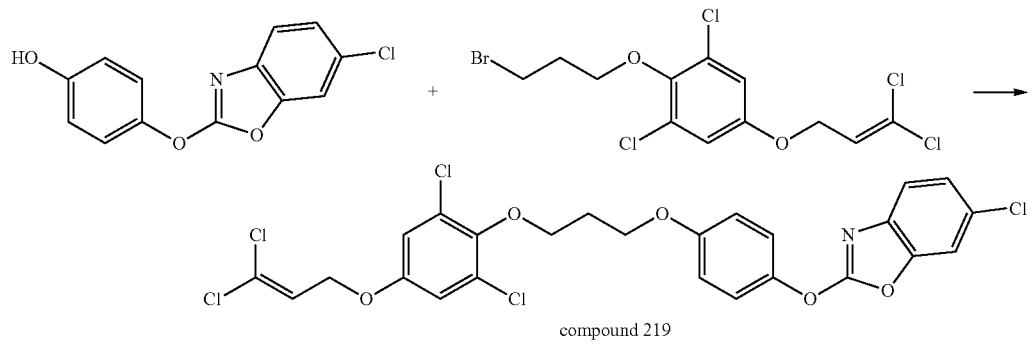

compound 219

The preparation process was the same as that in step (2) of example 1, only replacing 4-(3-chloro-5-(trifluoromethyl) pyridin-2-yloxy)phenol with 4-(6-chlorobenzo[d]oxazol-2-yloxy)phenol (0.39 g, 3 mmol), the residue was purified via silica gel column chromatography (Fluent: ethyl acetate/petroleum ether=1:30) to give the product (1.32 g) as pale yellow solid in 75% yield, imp. 80-82° C.

$^1$H-NMR spectrum (300 MHz, internal standard TMS, solvent CDCl$_3$) is as follows: δppm 7.44 (m, 2H), 7.39 (m, 1H), 7.31 (d, 2H), 6.99 (d, 2H), 6.84 (s, 2H). 6.12 (t, 1H), 4.58 (d, 2H), 4.28 (t, 2H), 4.18 (t, 2H), 2.31 (m, 2H).

Other compounds of the general formula (I) were prepared according to the above examples. Physical properties and $^1$H NMR spectrum of some compounds of this invention refer to Table 17.

TABLE 17

| No. | Melting point and $^1$HNMR spectrum ($^1$HNMR, 300 MHz, internal standard: TMS, solvent CDCl$_3$) |
|---|---|
| 3 | Oil, δppm7.90 (d, 1H), 7.50 (t, 1H), 7.10 (d, 2H), 6.96 (d, 2H), 6.84 (s, 2H), 6.10 (t, 1H), 4.58 (d, 2H), 4.18 (m, 4H), 2.30 (m, 2H) |
| 11 | Oil; δppm 7.89 (s, 1H), 7.14 (d, 2H), 7.07 (d, 2H), 6.84 (s, 2H), 6.12 (t, 1H), 4.58 (d, 2H), 4.22 (m, 4H), 2.31 (m, 2H) |
| 83 | Oil; δppm 7.89 (s 1H), 7.14 (d, 2H), 7.07 (d, 2H), 6.84 (s, 2H), 6.12 (t, 1H), 4.58 (d, 2H), 4.22 (m, 4H), 2.31 (m, 2H) |
| 84 | Oil; δppm 7.89 (s, 1H), 7.14 (d, 2H), 7.07 (d, 2H), 6.84 (s, 2H), 6.12 (t, 1H), 4.58 (d, 2H), 4.22 (m, 4H), 2.31 (m, 2H) |
| 117 | Oil; δppm 7.89 (s, 1H), 7.14 (d, 2H), 7.07 (d, 2H), 6.84 (s, 2H), 6.12 (t, 1H), 4.58 (d, 2H), 4.22 (m, 4H), 2.31 (m, 2H) |
| 118 | Oil; δppm 7.89 (s, 1H), 7.14 (d, 2H), 7.07 (d, 2H), 6.84 (s, 2H), 6.12 (t, 1H), 4.58 (d, 2H), 4.22 (m, 4H), 2.31 (m, 2H) |

FORMULATION EXAMPLE

Base on 100% Active Ingredient(Weight/Weight %)

| Example 8: 30% wettable powders | |
|---|---|
| Compound 1 | 30% |
| Sodium dodecyl sulfate | 2% |
| Lignin sultonate | 3% |
| Naphthalene sulfonic acid formaldehyde condensate | 5% |
| Precipitated calcium carbonate | Make up to 100% |

Compound 1 and other components are fully mixed, after smashing through ultrafine pulverizer, that is, 30% compound 1 wettable powders products.

| Example 9: 40% suspension concentrate | |
|---|---|
| Compound 2 | 40% |
| Glycol | 10% |
| Nonylphenols polyethylene glycol ether | 6% |
| Lignin sulfonate | 10% |
| Carboxymethyl cellulose | 1% |
| 37% formaldehyde aqueous solution | 0.2% |
| 75% of silicone oil water emulsion | 0.8% |
| Water | Make up to 100% |

Fully mixing compound 2 and other components, suspension concentrate can be obtained, and then any required concentration dilution can be obtained by diluting the above obtained concentrated suspension with water.

| Example 10: 60% water dispersible granules | |
|---|---|
| Compound 38 | 60% |
| Naphthalene sulfonate formaldehyde condensate | 12% |
| N-methyl-N-oil acyl-bovine sodium | 8% |
| Polyvinylpyrrolidone | 2% |
| Carboxymethyl cellulose | 2% |
| Kaolin | Make up to 100% |

Compound 38 and other components are fully mixed, after smashing, kneading together with water, added to the granulation 10-100 mesh machine for granulation, then by drying and sieving (at the scope screen).

| Example 11: 10% emulsifiable concentrate | |
|---|---|
| Compound 1 | 10% |
| Phenylethylphenol polyoxyethylene polyoxypropylene ether | 2% |
| styrylphenol polyoxyethylene ether | 3% |
| methanol | 6% |
| xylene | Make up to 100% |

Compound 1 and other components were sufficiently stirred and mixed to give 10% emulsifiable concentrate.

Test of Biological Activity

Example 12

Determination of Insecticidal Activity in Greenhouse

Determination of insecticidal activity of compounds of the present invention against a few insects were carried out by the following procedures:

Compounds were dissolved in mixed solvent (acetone:methanol=1:1), and diluted to required concentration with water containing 0.1% of tweed 80.

Diamond back moth, armyworm, beet armyworm and housefly were used in insecticidal activity test.

(1) Determination of Insecticidal Activity Against Diamond Back Moth

The method of spraying by airbrush: The cabbage leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25° C., 60~70% R.H.), Scores were conducted and mortalities were calculated after 72 h.

Part of test results against diamond back moth:

At 600 mg/L, compound 1, 2, 3, 11, 38, 57, 72, 80, 83, 84, 117, 118, 219 showed more than 80% control of the second instar larvae of diamond back moth, and compound 1, 2, 3, 11, 38, 57, 72, 80, 83, 117, 219 showed 100% control.

At 50 mg/L, compound 1, 2, 3, 11, 38, 80, 83 showed more than 80% control of the second instar larvae of diamond back moth, and compound 1, 2, 80 showed 100% control.

With reference to the above method, Compounds 1, 2, the known compound D-1 (compound 116 of WO9604228 (homemade, 96%)) and compound D-2 (Compound 36 of WO9611909 (commercially available standard product, 98%)) were carried out parallel determination againnst diamond back moth. The test results are shown in Table 18.

TABLE 18

Insecticidal activity against diamond back moth

| compounds | Mortality of diamond back moth (%) | | |
|---|---|---|---|
| | 50 mg/L | 25 mg/L | 6.25 mg/L |
| Compound 1 | 100 | 100 | 100 |
| Compound 2 | 100 | 100 | 75 |
| Compound D-1 | 80 | 30 | 0 |
| Compound D-2 | 90 | 75 | 50 |

(2) Determination of Insecticidal Activity Against Armyworm

The method of spraying by airbrush: The corn leaves were made into plates of 2 cm diameter by use of punch. A test solution (0.5 ml) was sprayed by airbrush at the pressure of 0.7 kg/cm$^2$ to both sides of every plate. 10 Second instar larvae were put into the Petri-dishes after the leaf disc air-dried and 3 replicates were set thr each treatment. Then the insects were maintained in observation room (25° C., 60~70% R.H.). Scores were conducted and mortalities were calculated after 72 h.

Part of test results against armyworm:

At 600 mg/L, compound 3, 11, 38, 57, 72, 80, 83, 84, 117, 118, 219 showed 100% control of the armyworm.

At 100 mg/L, compound 3, 11, 38, 57, 72, 80, 83, 84, 117, 118, 219 showed more than 90% control of the armyworm, and compound 38, 84, 117, 118, 219 showed 100% control.

With reference to the above method, compound 1, compound 117, compound 219 and the known compounds D-1 were carried out parallel determination against armyworm. The test results are shown in Table 19.

TABLE 19

Insecticidal activity against armyworm

| compounds | Mortality of armyworm (%) | |
|---|---|---|
| | 100 mg/L | 10 mg/L |
| Compound 1 | 100 | 100 |
| Compound 117 | 100 | 100 |
| Compound 219 | 100 | 70 |
| Compound D-1 | 90 | 30 |

(3) Determination of Insecticidal Activity Against Beet Armyworm 24 well-plate artificial diet emulsion method: artificial food was added to each well of the 24 well-plate, after the artificial food was cooled, the prepared solution were added into the 24 well-plate according to the experimental design by order of chemical concentrations from low to high, by gently shaking the even emulsion film can be formed on the surface of the diet. 24 neat and healthy larvae were put into the 24 well-plate (one larvae each well) after the film was air-dried and 3 replicates were set for each treatment. Then the insects were maintained in observation room (25° C., 60~70% R.H.). Scores were conducted and mortalities were calculated after 72 h.

With reference to the above method, compound 1 and the known compounds D-2 were carried out parallel determination against beet armyworm. The test results are shown in Table 20.

TABLE 20

Insecticidal activity against beet armyworm

| compounds | Mortality of beet armyworm (%) | |
|---|---|---|
| | 10 mg/L | 2.5 mg/L |
| Compound 1 | 100 | 47.8 |
| Compound D-2 | 100 | 16.7 |

(4) Determination of Insecticidal Activity Against Housefly

Diet Incorporation Tests: the test compound was dissolved with 90% acetone to obtain the mother liquor after weigh accurately with an electronic balance. The required concentration solution was got by diluting to the mother liquor with a certain concentration milk powder solution according to the designed doses in the experiment. Then, the diluted concentration solution was evenly put into the petri dishes with diameter of 6 cm inside which filter paper was placed by using a transferring-liquid gun (Ira, solution each petri dish). Finally the 3$^{rd}$ instars of larvae were put into petri dishes with 10 each petri dish, and 3 replicates were set for each treatment. Then the insects were maintained in observation room (25° C., 60~70% R.H.). Scores were conducted and mortalities were calculated after 72 h.

With reference to the above method, compound 1 and the known compounds D-2 were carried out parallel determination against housefly. The test results are shown in Table 21.

TABLE 21

Insecticidal activity against housefly

| compounds | Mortality of housefly (%) | |
|---|---|---|
| | 20 mg/L | 10 mg/L |
| Compound 1 | 100 | 66.7 |
| Compound D-2 | 25 | 0 |

Example 13

Field Trial

(1) Field Trial Against Beet Armyworm on Cabbage

The trial was carried out in rain shelter area of experimental field of Wuhan vegetable research institute, the test crop is cabbage (variety: Jingfeng NO. 1). The dosage of the invention compound 1 (Example 11, 10% EC, same as below) are 75, 105, 150 g a.i./hm$^2$. and the comparative agent pyridalyl (10% EC, commercially available, same as below) is 105 g a.i./hm$^2$. The agent was applied on 9 Oct. 2011. The application tool is Linong 16HD-400 type backpack spray. Evenly spraying to whole cabbage which is in rosette stage was conducted. Beet armyworm is mainly larvae. The plot area is 25 m$^2$ and 4 replicates and randomized block arrangement were set. The amount of spray liquid is 750 L/hm$^2$. It was sunny and there was no wind, with the highest temperature of 28° C. and the lowest of 15° C. on the day of the application. Chosen 10 plants from each plot and scored the larvae at different instars at fixing time. The base number was investigated before treatment. The number of living larvae was counted after 1 day, 3 days, 7 days and 14 days respectively after application and control efficacy was calculated.

Calculation Method:

Decrease rate of insects (%)=(the number of insects before application–the number of insects after application) the number of insects before application×100

Control efficacy (%)=(decrease rate of insects in treated area decrease rate of insects in blank comparative area)/(100–decrease rate of insects in blank comparative area)×100

Control efficacy is as follows:

TABLE 22

The results of the field trial of compound 1 against beet armyworm on cabbage

| compounds | Dosage (g a.i./hm²) | Control efficiency (%) | | | |
|---|---|---|---|---|---|
| | | 1 day after treatment | 3 days after treatment | 7 days after treatment | 14 days after treatment |
| Compound 1 | 75 | 63.18 | 86.14 | 80.51 | 73.51 |
| | 105 | 69.20 | 92.30 | 86.19 | 83.69 |
| | 150 | 71.17 | 94.09 | 90.45 | 88.42 |
| pyridalyl | 105 | 70.76 | 83.34 | 78.33 | 61.21 |

(2) Field Trial Against Diamond Back Moth on Cabbage

The trial was carried out in the test filed of Shenyang Research Institute of Chemical industry Ltd. The trial crop is cabbage (Variety: Zhonggan NO 8.). The dosage of the compound 1 are 75, 105, 150 g a.i./hm² and comparative agent pyridalyl is 105 g a.i./hm². The agent was applied once on 13 Jun. 2011. The application tool is Shandongweishi WS-16P type backpack manual sprayer. Evenly spraying to whole cabbage which is in rosette stage was conducted. Diamond back moth is originated at the peak time. The plot area is 10 m², 3 replicates and randomized block arrangement were set. The amount of spray liquid is 750 L/hm². It was sunny with the highest temperature of 29° C., and the lowest of 17° C. on the day of the application of the spray. The methods of investigation and calculation are the same as Example 13.

Control efficacy is as follows:

TABLE 23

The control efficacy of Compound 1 against diamond back moth on Cabbage

| compounds | Dosage (g a.i./hm²) | Control efficacy (%) | | |
|---|---|---|---|---|
| | | 1 day after treatment | 3 days after treatment | 7 days after treatment |
| Compound 1 | 75 | 86.0 | 98.7 | 97.6 |
| | 105 | 93.4 | 97.0 | 97.8 |
| | 150 | 90.4 | 97.9 | 97.9 |
| pyridalyl | 105 | 95.1 | 97.0 | 94.9 |

(3) Field Trial Against Cabbage Butterfly (*Pierisrapae Linne*)

The trial was carried out in a farmer's vegetable field in Xiangcheng District Suzhou City. The variety of the cabbage is Xinxia 50. The dosage of the compound 1 are 75, 105, 150 g a.i./hm² and the comparative agent pyridalyl is 105 g a.i./hm². The agent was applied on 26 May 2011. The application tool is Singaporean Linong HD-400 type backpack spray. Evenly spraying to whole cabbage which is at vegetative growth phase was conducted, Cabbage butterfly is at a peak time of 1-3 instars of larvae. The plot area is 15 m², 4 replicates and randomized block arrangement were set. The amount of spray liquid is 750 L/hm². It was from sunny to cloudy with the highest temperature of 22.6° C., and the lowest of 17.8° C. on the day of the application of the spray. Chosen 10 plants from each plot and scored the larvae at different instars at fixing time. The base number was investigated before treatment. The number of living larvae was counted after 1 day, 4 days, 7 days and 12 days respectively after application and control efficacy was calculated.

Calculation method: the same as Example 13. The Control efficacy is as follows:

TABLE 24

The results of the field trial of compoud 1 against cabbage butterfly

| compounds | Dosages (g a.i./hm²) | Control efficiency (%) | | | |
|---|---|---|---|---|---|
| | | 1 day after treatment | 4 day after treatment | 7 day after treatment | 12 days after treatment |
| Compound 1 | 75 | 40.4 | 84.1 | 86.7 | 81.2 |
| | 105 | 44.0 | 87.9 | 92.6 | 85.0 |
| | 150 | 45.2 | 89.6 | 92.8 | 85.4 |
| pyridalyl | 105 | 49.7 | 84.3 | 88.5 | 75.8 |

What is claimed is:

1. An aryloxy dihalopropenyl ether compound having general formula (I):

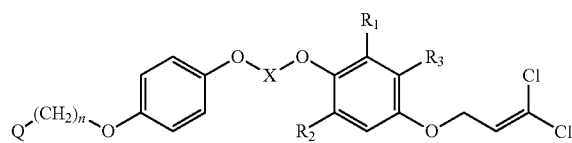

(I)

wherein:
$R_1$, $R_2$, $R_3$ mutually independently may be the same or different, selected from H or Cl;
X is —$CH_2CH_2CH_2$—;
Q is selected from thiazolyl, pyridinyl, pyridazinoneyl, or benzoxazolyl or above group substituted with 1-3 substitutents mutually independently selected from F, Cl, Br, $CH_3$, $C_2H_5$, $C(CH_3)_3$, $CF_3$, $CHFCH_3$ or $CHF_2$;
n is selected from 0 or 1.

2. The compound according to the claim 1, characterized in that wherein general formula (I):
Q is selected from pyridinyl or pyridinyl substituted with 1-3 substituents mutually independently selected from F, Cl, Br, or $CF_3$;
n is selected 0.

3. A method of controlling insects which comprises applying the compound having general formula (I) according to claim 1 to agricultural and other fields.

4. An insecticidal composition comprising the compound having general formula (I) of claim 1 as an active ingredient, and a solvent medium and/or a solid diluent and/or additives, wherein the weight percentage of the active ingredient in the composition is from 0.1-99%.

5. A method of controlling insects which comprises applying the compound having general formula (I) according to claim 2 to agricultural and other fields.

\* \* \* \* \*